US009636176B2

(12) United States Patent
Hancock et al.

(10) Patent No.: US 9,636,176 B2
(45) Date of Patent: May 2, 2017

(54) ELECTROSURGICAL INSTRUMENT WITH DUAL RADIOFREQUENCY AND MICROWAVE ELECTROMAGNETIC ENERGY

(75) Inventors: Christopher Paul Hancock, Bath (GB); Martin Wynford Booton, Wells (GB)

(73) Assignee: CREO MEDICAL LIMITED, Chepstow (GB)

( * ) Notice: Subject to any disclaimer, the term of this patent is extended or adjusted under 35 U.S.C. 154(b) by 176 days.

(21) Appl. No.: 13/997,915

(22) PCT Filed: Jan. 9, 2012

(86) PCT No.: PCT/GB2012/050034
§ 371 (c)(1),
(2), (4) Date: Jun. 25, 2013

(87) PCT Pub. No.: WO2012/095653
PCT Pub. Date: Jul. 19, 2012

(65) Prior Publication Data
US 2013/0289557 A1 Oct. 31, 2013

(30) Foreign Application Priority Data
Jan. 11, 2011 (GB) .................... 1100444.7

(51) Int. Cl.
*A61B 18/18* (2006.01)
*A61B 18/14* (2006.01)
(Continued)

(52) U.S. Cl.
CPC ......... *A61B 18/1815* (2013.01); *H01Q 13/08* (2013.01); *H01Q 21/06* (2013.01);
(Continued)

(58) Field of Classification Search
CPC ............... A61B 18/18; A61B 18/1815; A61B 2018/1876; A61B 2018/1892; H01Q 13/06; H01Q 13/08
(Continued)

(56) References Cited

U.S. PATENT DOCUMENTS 5,336,222 A 8/1994 Durgin, Jr. et al.
2006/0259024 A1* 11/2006 Turovskiy et al. ............. 606/33
(Continued)

FOREIGN PATENT DOCUMENTS

EP 2 253 286 A1 11/2010
JP 2005-512726 A 5/2005
(Continued)

OTHER PUBLICATIONS

Japanese Office Action mailed Nov. 10, 2015 for Japanese Patent Application No. 2013-548887, with English Translation.

*Primary Examiner* — Michael Peffley
*Assistant Examiner* — Khadijeh Vahdat
(74) *Attorney, Agent, or Firm* — Arent Fox LLP

(57) ABSTRACT

An electrosurgical instrument for delivering radiofrequency (RF) electromagnetic (EM) energy and microwave frequency EM energy from a coaxial feed cable through an instrument tip into tissue. The instrument tip comprises a dielectric body separating first and second conductive elements, which act as active and return electrodes to convey the RF EM radiation by conduction, and as an antenna to radiate the microwave EM radiation. The instrument also has a fluid feed incorporated into its tip, e.g. in an additional dielectric element mounted on the underside of the tip, for delivering fluid. The delivered fluid may be a gas plasma to assist treatment or a liquid to plump up a tissue region before treatment. The instrument may fit in an endoscope.

15 Claims, 14 Drawing Sheets

(51) Int. Cl.
*H01Q 13/08* (2006.01)
*H01Q 21/06* (2006.01)

(52) U.S. Cl.
CPC ................ *A61B 2018/1876* (2013.01); *A61B 2018/1892* (2013.01)

(58) Field of Classification Search
USPC ..................................................... 606/33–41
See application file for complete search history.

(56) References Cited

U.S. PATENT DOCUMENTS

| | | | |
|---|---|---|---|
| 2008/0076958 A1 | 3/2008 | Britva et al. | |
| 2009/0005771 A1 | 1/2009 | Lieber et al. | |
| 2010/0030207 A1 | 2/2010 | Hancock | |
| 2010/0042095 A1 | 2/2010 | Bigley et al. | |
| 2010/0125269 A1* | 5/2010 | Emmons et al. | 606/33 |
| 2010/0296977 A1 | 11/2010 | Hancock | |
| 2010/0298822 A1* | 11/2010 | Behnke | 606/33 |
| 2013/0267943 A1* | 10/2013 | Hancock | A61B 18/042 606/33 |

FOREIGN PATENT DOCUMENTS

| | | |
|---|---|---|
| JP | 2009-056290 A | 3/2009 |
| JP | 2010-269148 A | 12/2010 |
| WO | WO 03/055402 A1 | 7/2003 |

\* cited by examiner

ELECTROSURGICAL INSTRUMENT WITH DUAL RADIOFREQUENCY AND MICROWAVE ELECTROMAGNETIC ENERGY

CROSS-REFERENCE TO RELATED APPLICATIONS

This application is a National Stage entry of International Application PCT/GB2012/050034 filed Jan. 9, 2012, which claims priority of United Kingdom Application No. 1100444.7 filed Jan. 11, 2011, the disclosure of these prior applications are hereby incorporated in their entirety by reference.

TECHNICAL FIELD

The invention relates to instruments for use with electrosurgical apparatus in which radiofrequency and microwave frequency energy is used to treat tissue. In particular, the invention relates to electrosurgical instruments capable of emitting radiofrequency energy for cutting tissue and microwave frequency energy for haemostasis (i.e. sealing broken blood vessels by promoting blood coagulation).

BACKGROUND TO THE INVENTION

Surgical resection is a means of removing sections of unwanted tissue associated with organs within the human or animal body, such as the liver or the spleen or the bowel. When tissue is cut (divided or transected) small blood vessels called arterioles are damaged or ruptured. Initial bleeding is followed by a coagulation cascade where the blood is turned into a clot in attempt to plug the bleeding point. During an operation, it is desirable for a patient to lose as little blood as possible, so various devices have been developed in an attempt to provide blood free cutting.

For example, the Hemostatix® Thermal Scalpel System (http://www.hemostatix.com) combines a sharp blade with a haemostatic system. The blade is coated with a plastic material and connected to a heating unit which accurately controls the temperature of the blade. The intention is for the heated blade to cauterise the tissue as it is cut.

Other known devices that cut and stop bleeding at the same time do not use a blade. Some devices use radiofrequency (RF) energy to cut and/or coagulate tissue. Other devices (known as harmonic scalpels) uses a rapidly vibrating tip to cut tissue.

The method of cutting using RF energy operates using the principle that as an electric current passes through a tissue matrix (aided by the ionic contents of the cells), the impedance to the flow of electrons across the tissue generates heat. When a pure sine wave is applied to the tissue matrix, enough heat is generated within the cells to vaporise the water content of the tissue. There is thus a huge rise in the internal pressure of the cell, that cannot be controlled by the cell membrane, resulting in the cell rupturing. When this occurs over a wide area it can be seen that tissue has been transected.

RF coagulation operates by applying a less efficient waveform to the tissue, whereby instead of being vaporised, the cell contents are heated to around 65° C. This dries out the tissue by desiccation and also denatures the proteins in the walls of vessels and the collagen that makes up the cell wall. Denaturing the proteins acts as a stimulus to the coagulation cascade, so clotting is enhanced. At the same time the collagen in the wall is denatured from a rod like molecule to a coil, which causes the vessel to contract and reduce in size, giving the clot an anchor point, and a smaller area to plug.

WO 2008/044000 discloses surgical resection apparatus adapted to simultaneously cut and seal highly vascularised tissue, such as the liver or spleen. The apparatus comprising a source of microwave radiation that is coupled to a surgical instrument having an antenna associated with a blade for cutting biological tissue, wherein the antenna is arranged to controllably deliver microwave energy from the source to a region where the blade cuts through tissue. The microwave energy can coagulate blood to effectively seal off the blood flow at the cutting region. WO 2008/044000 suggests the use of high microwave frequencies (e.g. 10 GHz or higher), which offer a particular advantage over the use of known lower microwave frequency systems and radiofrequency (RF) systems due to the limited depth of penetration of the energy by radiation and the ability to enable small sharp blade structures to radiate energy efficiently into the tissue to seal off blood flow by being able to produce uniform fields along the length of the blade whilst at the same time being capable of cutting through the tissue to remove sections of diseased or cancerous tissue.

U.S. Pat. No. 6,582,427 discloses an electrosurgery system arranged to generate both RF energy (typically having a frequency of 1 MHz) and microwave energy (typically having a frequency of 2.45 GHz) for selective operation in a cutting mode or a coagulation mode.

SUMMARY OF THE INVENTION

The present disclosure describes developments of a concept put forward in the applicant's earlier UK patent application no. 0912576.6, filed on 20 Jul. 2009, which is described briefly below with reference to FIGS. 1 and 2.

The developments can be expressed as two aspects of the invention. At its most general, a first aspect of the invention provides an electrosurgical instrument capable of delivering both radiofrequency (RF) electromagnetic (EM) energy and microwave frequency EM energy into tissue in which a fluid feed is incorporated into the instrument tip to permit delivery of fluid (e.g. gas or liquid) thereto. The gas or liquid may be delivered out of the instrument, e.g. as a gas plasma to assist treatment or as a liquid to "plump" up a tissue region before treatment, e.g. to raise a polyp that sits on the wall of the bowel to assist in its removal without causing damage to the bowel wall. The instrument may reach the treatment site through an endoscope, whereby the fluid may also be used to flush the treatment site (e.g. bowel), e.g. to remove debris from the viewing instrumentation (camera or lens) contained within the endoscope. The fluid may be delivered simultaneously with or separately from the RF and microwave frequency EM radiation.

Thus, according to the first aspect, there may be provided an electrosurgical resection instrument for applying to biological tissue radiofrequency (RF) electromagnetic (EM) energy having a first frequency and microwave EM energy having a second frequency higher than the first frequency, the instrument comprising: a instrument tip comprising a body made of a first dielectric material separating a first conductive element from a second conductive element; a coaxial feed cable comprising an inner conductor, an outer conductor coaxial with the inner conductor, and a second dielectric material separating the outer and inner conductors, the coaxial feed cable being for conveying, simultaneously or separately, an RF signal having the first frequency and a microwave signal having the second frequency; and a fluid feed conduit for delivering fluid to the instrument tip; wherein the inner conductor is electrically connected to the first conductive element and the outer conductor is electrically connected to the second conductive element to enable the instrument tip to receive the RF signal and the microwave signal, and wherein the first and second conductive elements are arranged to act: as active and return electrodes to convey RF EM radiation corresponding to the RF signal by conduction, and as an antenna to radiate microwave EM radiation corresponding to the received microwave signal.

The instrument may be configured to provide a local return path for RF energy, i.e. a low impedance route for RF energy to be transported between the first and second conductive elements. For example, the first dielectric material separating the conductive elements may provide a local return path, or, as explained below, a gas may be delivered to the instrument tip to permit a plasma to be generated in the vicinity of the conductive elements to provide the local low impedance return path. RF tissue cutting may be produced at an edge of the instrument tip if the first dielectric material has a high dielectric constant (e.g. greater than that of air) and where the separation of the first and second conductive elements by the first dielectric material at that edge is small, i.e. less than 1 mm. This arrangement may provide the necessary preferential return path for the current to flow.

The instrument may be suitable for use with electrosurgical resection apparatus to carry out open and key-hole or laparoscopic procedures under local anaesthetic that are currently performed in an open environment under general anaesthetic.

The fluid feed conduit may be arranged to deliver liquid (e.g. saline) to the instrument tip, the fluid feed conduit having an outlet at the distal end of the instrument tip for introducing the liquid into the biological tissue. Injection of fluid (saline or the like) to plump up the biological tissue may be particularly useful where the instrument is to treat the wall of the bowel. Plumping up the tissue in this manner may help to reduce risk of bowel perforation. It is advantageous to be able to use same instrument to deliver fluid as delivers RF and/or microwave energy since deflation (e.g. due to fluid seepage) may occur if a separate instrument is introduced into the region or during treatment. The ability to introduce fluid using the same treatment structure enables the level to be topped up as soon as deflation occurs. Moreover, the use of a single instrument to perform desiccation or dissection as well as to introduce fluid also reduces the time taken to perform the overall polyp removal procedure, reduces the risk of causing harm to the patient and also reduces the risk of infection. More generally, injection of fluid may be used to flush the treatment region, e.g. to remove waste products or removed tissue to provide better visibility when treating. As mentioned above, this may be particularly useful in endoscopic procedures.

The underside of the instrument tip body may have a convex or curved profile in width and may curve upwards slightly along the length in order to reduce the risk of the instrument digging into the bowel wall and causing a bowel perforation. The instrument may comprise a third dielectric material (e.g. ceramic) attached (e.g. bonded) to the second conductive element on the opposite side to the first dielectric material. The third dielectric material may be shaped (e.g. moulded) to form the curved underside.

The fluid feed conduit may terminate (e.g. at its distal end) with a rigid tube or needle, e.g. hypodermic needle, which may have a smaller diameter than the remainder of the fluid feed conduit. The rigid tube or needle preferably includes a penetrating distal portion suitable for piercing biological tissue. The fluid feed conduit may be mounted on the underside of the instrument, e.g. separately from the first and second conductive elements. For example, the fluid feed conduit may be mounted in or on the third dielectric material, whereby the fluid may be introduced from the curved section of the instrument. This device structure may be particularly useful for the removal of sessile polyps that sit on the wall of the bowel. The material used to construct the curved section and house the needle or tube does not need to be a low loss microwave material like that used to propagate the microwave and RF field since it is not involved in the propagation of the electromagnetic field. Suitable materials are: ceramic, biocompatible plastics that do not stick to the wall of the bowel (or other biological tissue) or the like. The material should be arranged to allow the device to be curved both in width and along its length. It may be preferable to start the curve around halfway, e.g. 4 mm or 5 mm along the length so that the proximal end (where the RF and/or microwave radiation is fed into the instrument tip body) is flat and the distal end is raised. This configuration further reduces the risk of the device causing bowel perforation during the polyp removal process.

In one embodiment, the fluid feed conduit may be movable longitudinally relative to the instrument tip body, e.g. to protrude from or retract into the instrument tip. A protruding portion of the fluid feed conduit may comprise the rigid tube or needle mentioned above.

The coaxial feed cable and the fluid feed conduit may be conveyed to the instrument tip body in a common carrier tube. The common carrier tube may comprise a tubular body dimensioned to fit in the instrument channel of an endoscope, which tubular body has a pair of longitudinally extending bores formed therein for receiving the coaxial feed cable and fluid feed conduit respectively.

The proximal end of the fluid feed conduit may terminate with a connector that allows it to be attached to a syringe used to store and introduce liquid into the pipe. The syringe may be located near the controls used to manipulate or control the movement of the endoscope.

Alternatively or additionally, the fluid feed conduit may be arranged to deliver gas into a plasma generation region located between the first and second conductive elements in the instrument tip, and wherein the first and second conductive elements are configured to create an electric field from the received RF signal and/or microwave signal that is capable of ionising the gas to generate a thermal or non-thermal plasma. The gas may be air or a suitable inert gas (e.g. argon) or a mixture of gases. The plasma generation region may be enclosed within the instrument tip, wherein the plasma is used to provide a local return path for the RF signal to facilitate cutting the biological tissue.

The plasma may assist in providing the preferential return path for the RF current by setting up conducting plasma between the first and second conductive elements and/or to generate and emit thermal plasma to assist with the cutting and/or sealing and/or to coagulate the surface of the tissue, i.e. in a manner similar to argon beam coagulation.

For instruments having a small diameter (e.g. 2.5 mm or less) and long length (e.g. 1 m or more) the thermal and/or non-thermal plasma may be induced by the microwave frequency EM energy. This is preferably because the ability to strike and sustain plasma is not limited by the capacitance of the cable and the need to produce very high voltages at the generator end, which may be necessary for RF-generated plasmas. The microwave cable offers a fixed impedance environment and the ability to multiply the field using quarter wave structures (transformers) means that consistent plasma can be formed with relatively low levels of microwave power.

Alternatively, the plasma generation region may include an outlet for permitting non-thermal or thermal plasma to be delivered to the biological tissue. Non-thermal plasma can be used to sterilise tissue, which may be of particular interest in applications relating to the emerging NOTES technology, where it could be advantageous to be able to sterilise a range of natural orifices. Thermal plasma can be used to perform surface coagulation/ablation or tissue cutting.

The plasma may be generated using the RF EM energy delivered to the instrument tip, the microwave frequency energy or a combination of both. In one embodiment, a pulse of RF EM energy may be used to strike the plasma, which is subsequently sustained by the microwave frequency energy. Techniques for creating a plasma in an electrosurgical instrument are disclosed in WO 2009/060213, which is incorporated herein by reference.

The instrument tip may have any one of four structures described herein:
 a unitary body (i.e. single piece of metallised dielectric material, e.g. ceramic or the like) suitable for use in open surgery and key-hole (laparoscopic) surgery;
 a coaxial structure in which the first conductive element is an inner conductor, the second conductive element is an outer conductor coaxial with the inner conductor and separated therefrom by the body of first dielectric material; and
 a parallel plate structure (i.e. a planar transmission line element) in which the body of first dielectric material is a substantially planar element, the first conductive element is a first conductive layer on a first surface of the planar element, and the second conductive element is a second conductive layer on a second surface of the planar element that is opposite to the first surface.

The unitary body may have a shape that conforms to a treatment target area or to perform a desired function. For example, the instrument tip may be curved to follow the wall of the bowel, or may be hooked to facilitate tissue removal. These ideas are discussed below in relation to the second aspect of the invention.

Where the coaxial structure mentioned above is used, the fluid feed conduit may include a hollow passageway incorporated in the coaxial feed cable and the coaxial structure. For example, the gas can be introduced into the instrument tip along a hollow inner conductor, or between the inner and outer conductors.

Where the planar transmission line element mentioned above is used, the fluid feed conduit may be arranged to introduce gas between the first and second conductive layers (which may be formed a two independent plates) to create non-thermal or thermal plasma that can be used to provide the return path for the RF current or sterilise tissue, or cut tissue. The planar transmission line element may contain a both a region of dielectric material with a high dielectric constant to provide the local return path and a second open region that can be filled with gas to enable non-thermal plasma to be produced to sterilise tissue or for thermal plasma to be produced for tissue cutting or surface coagulation to be performed. This arrangement may also take advantage of the use of a material with a high relative permittivity (or dielectric constant) inserted between the two conductive layers or plates (active and return conductors). The high permittivity material increases the capacitance of the structure, which in turn reduces the impedance of the structure in a linear manner, thus helping to ensure that the preferential return path for the RF current is set up or exists between the two plates.

When the plasma is removed, the structure looks like a parallel plate transmission line with air separating the two plates. This arrangement may be used to efficiently radiate microwave energy along one or more of the edges of the structure and/or through a single or plurality of slots or apertures contained within one or more of the surfaces. The parallel plate structure without plasma may also be used to set-up the conditions necessary for RF cutting and microwave coagulation, i.e. at RF the structure can be modelled as a parallel plate capacitor with a dielectric material sandwiched between the two plates with layers of metallization coming to the edges along the length of the blade and cut back at the ends and at microwave frequency, the structure may be modelled as a distributed element transmission line structure capable of radiating microwave energy from one or both long edges and/or from the distal end.

The parallel plate structure with a layer of metallization on both sides of the dielectric material may be used to efficiently perform RF tissue cutting in a most efficient manner when the respective layer of metallization comes right to the edge of the dielectric material, i.e. no dielectric material is exposed on the surfaces and only metal can be seen. The dielectric can also be exposed such that microwave ablation or coagulation can be performed along the edges or at the end of the structure.

It may be preferable to remove a small amount of metallization at the distal end of the structure, i.e. 0.5 mm to 1 mm from the end, in order to prevent the device from cutting into tissue at the end if that is undesirable (although the invention is not necessarily limited to devices which do not cut at the distal end of the instrument tip). However, a structure that can deliver microwave energy for coagulation, but no RF energy for cutting at the end of the blade is preferable for applications relating to bowel surgery, i.e. for the removal of sessile polyps, since this arrangement reduces the risk of bowel perforation.

In one embodiment, the parallel plate structure may be configured as follows:
 (i) first dielectric material comprises a block having a width of 1.5 mm to 2 mm, length of 6 mm to 12 mm;
 (ii) the first and second conductive elements comprise layers of metallization on the opposite surfaces of the first dielectric material that extends to the edges on both sides of the dielectric along the length of the blade, the overall thickness of the block with layers of metallization being 0.3 mm to 0.5 mm;
 (iii) a 0.5 mm gap in the metallization forming the first conductive element at the proximal end of the first dielectric material for matching and to prevent the active conductor being shorted out;
 (iv) a 0.2 mm to 1 mm gap in the metallization forming the first and second conductive elements at the distal end of the first dielectric material to prevent the structure from cutting tissue; and
 (v) a small radius of approximately 0.2 mm on the corners of the distal end of the first dielectric material to prevent the structure from getting stuck inside the instrument channel of the endoscope due to the sharp edges snagging on the inner walls.

Where the device is used to emit plasma, a slot or plurality of slots may be provided to allow the hot gas to escape from the structure to create the desired tissue cutting effect. Non-thermal plasma may also be radiated from said slots in order to enable the same device to be used to sterilise tissue or kill bacteria within or on the surface of tissue located in the vicinity of the applicator, i.e. within a natural orifice or on the surface of an organ, e.g. the liver.

The instrument tip may comprise a plurality of planar transmission line elements arranged in parallel, the plurality of planar transmission line elements received the RF signal and the microwave signal from the coaxial feed cable via a balanced power splitter arrangement. The balanced power splitter may ensure that the RF and microwave signals are received by plurality of transmission line elements in phase, so that the total emitted energy is uniform.

The instrument tip may include a quarter wavelength transformer (i.e. a connector having an electrical length equal to an odd multiple of a quarter of the wavelength at the frequency of operation) connected between the coaxial feed cable and the plurality of planar transmission line elements to impedance match the coaxial feed cable to the plurality of planar transmission line elements.

The coaxial feed cable and fluid feed conduit have a combined diameter that is less than 2.5 mm, and the instrument tip may extend out of the coaxial feed cable by 8 mm or less (preferably 5 mm or less), and may have a width of 1.8 mm or less (preferably 1.5 mm or less) and a thickness of 0.5 mm or less (preferably 0.3 mm).

It may be noted that the invention is not limited to radiating only microwave energy at the end to coagulate tissue. In certain clinical applications it may be desirable to radiate both RF and microwave energy at the end or it may be desirable to radiate RF energy only. The same also applies to the two long edges and the two faces.

The instruments according to the first aspect are thus capable of accommodating the following inputs: RF EM energy, microwave frequency EM energy, and fluid (gas or liquid). The instrument may be configured to produce any one or more of the following clinical outputs:
  RF EM energy alone to cut biological tissue or perform surface ablation/coagulation;
  RF EM energy in conjunction with a non-thermal or thermal plasma (produced by the RF EM energy and/or the microwave frequency energy) to cut biological tissue (wherein the plasma is used to form the return path for the RF EM energy and the RF EM energy itself is used to burst the cells);
  thermal plasma produced by RF EM energy and/or microwave frequency energy to cut biological tissue;
  non-thermal produced by RF EM energy and/or microwave frequency energy to sterilize tissue; and
  microwave energy alone to seal/coagulate or ablate biological tissue.

If a gas plasma is set up between the active and return electrodes (first and second conductive elements) of the instrument, it may be switchable between performing RF cutting and the microwave sealing/coagulation.

The first and second conductive elements may form a bipolar emitting structure. The bipolar emitting structure may include a balun in the instrument tip to prevent sheath currents and ensure that the microwave frequency EM field is radiated in an outwardly direction. The balun may be a simple third conductor electrically connected (e.g. soldered) to the second conductor at the distal end to form a short circuit. By making the balun a quarter-wavelength long (at the microwave frequency of operation), the short circuit condition will be transformed to an open circuit condition to prevent the flow of current along the cable. A plurality of baluns may be provided in the instrument to increase the return loss when the instrument is inserted into tissue. For example, one balun may increase the return loss from 15 dB to 25 dB, two baluns may take it to 40 dB and three baluns may increase it to 60 dB, i.e. one millionth of the energy emanating from the instrument is being reflected back along the cable.

At its most general, a second aspect of the invention provides an electrosurgical instrument having a planar instrument tip capable of delivering both radiofrequency (RF) electromagnetic (EM) energy and microwave frequency EM energy into tissue in a targeted manner through suitable configuration of a pair of conductive elements on the instrument tip. In particular, this aspect of the invention permits inhibiting delivery of the RF EM energy except at a side edge of the planar instrument tip that is designated as a cutting edge. The invention is based on the inventors' realisation that the ability to deliver RF energy into tissue is dependent on the distance of metallization to the edges of the structure. In certain procedures it may be preferable to inhibit RF cutting along one or both edges, but deliver RF energy from the distal end.

Thus, according to the second aspect of the invention, there may be provided an electrosurgical resection instrument for applying to biological tissue radiofrequency (RF) electromagnetic (EM) energy having a first frequency and microwave EM energy having a second frequency higher than the first frequency, the instrument comprising: a instrument tip comprising a planar body made of a first dielectric material having a first conductive layer on a first surface and a second conductive layer on a second surface opposite the first surface; a coaxial feed cable comprising an inner conductor, an outer conductor coaxial with the inner conductor, and a second dielectric material separating the outer and inner conductors, the coaxial feed cable being for conveying, simultaneously or separately, an RF signal having the first frequency and a microwave signal having the second frequency; and wherein the inner conductor is electrically connected to the first conductive layer and the outer conductor is electrically connected to the second conductive layer to enable the instrument tip to receive the RF signal and the microwave signal, wherein the first and second conductive layers are arranged to act: as active and return electrodes to convey RF EM radiation corresponding to the RF signal by conduction, and as an antenna to radiate microwave EM radiation corresponding to the received microwave signal, and wherein first and second conductive layers may be set back from the edges of the planar body except at an RF cutting portion located along an edge of the planar body where it is desirable to perform tissue cutting.

This aspect of the invention makes use of the ability of the instrument to be "seen" differently by RF signal and microwave signal generating apparatus for the signals at the first and second frequencies. At the first frequency, the instrument tip may be modelled as a parallel plate capacitor. The electric field set up by the RF signal between the first and second conductive layers can be substantially contained with the planar body (first dielectric material) by setting the edges of the first and second conductive layers back from the side edges of the planar body. To perform RF cutting, it is desirable for the field to extend outside the planar body. In this invention it is possible to do this be extending the edges of the first and second conductive layers up to the side edge of the planar body in a region designated as an RF cutting portion. It may be preferable for this to be a side single side edge of the planar body; the first and second conductive layers may be set back from the distal edge and the side edge opposite to the RF cutting portion.

Meanwhile, at the second frequency, the instrument tip may be modelled as a parallel plate transmission line with the planar body representing dielectric material separating two conductive plates. The radiation pattern of the microwave frequency EM energy in this case depends on the overall shape of the planar body and the microwave feed structure. In this particular instance, the gap at the proximal end between the co-axial feed line (centre conductor) and the upper conductive layer plays an important role in ensuring that the microwave energy from the source is matched in terms of impedance with the load impedance presented by the tissue. Using known simulation tools, this may be modelled to control from which edges the microwave frequency EM energy is radiated. For example, the instrument tip may be configured to inhibit radiation of the microwave EM radiation from a distal edge of the planar body.

The side edge of the planar body having the RF cutting portion may have a hooked shape to facilitate tissue removal. It may also offer the ability to drag tissue back to enable the surgeon to have a greater level of control. The hooked shape may includes a substantially proximally facing tissue engagement portion. The hooked portion may comprise a smooth curve. The RF cutting portion is locating further from the distal end of the planar body than the substantially proximally facing tissue engagement portion, i.e. on the inside of the hooked shape.

The instrument may include a fluid feed conduit for delivering liquid (e.g. saline) to the instrument tip, wherein the fluid feed conduit has an outlet adjacent to the distal end of the planar body for introducing the liquid into the biological tissue.

The fluid feed may be integrated into a curved or convex section of material attached to the underside of the aforementioned planar structure. The radius of the curve may be such that it helps to ensure that the device does not perforate the bowel wall during operation, i.e. the curved shape prevents the device from digging into the bowel wall in such a manner that perforation may occur. The feed tube may terminate at the proximal end of the curved section, i.e. close to the point where the microwave/RF energy delivery cable enters the structure, with a needle structure that may have an outside diameter less than 0.6 mm, e.g. 0.4 mm. The needle may be introduced or retracted by movement of the fluid feed tube at the proximal end (where it may be attached to a syringe used to introduce fluid into the tube) or by using one or more control wires. As in the first aspect, the coaxial feed cable and the fluid feed conduit may be conveyed to the instrument tip body in a common carrier tube. The common carrier tube may comprise one or more additional bores for conveying the control wires to the instrument tip body. As mentioned above, the diameter of the common carrier tube is preferably less than 2.5 mm to enable it to fit down the instrument channel of an endoscope.

The fluid feed conduit may include a hollow passageway formed in the planar body, and the outlet may be a hole in the distal end of the planar body. The fluid feed conduit may include a flexible tube having an outer diameter of less than 1 mm that runs into the instrument tip alongside the coaxial feed cable, (which may be a microwave cable (e.g. Sucoform 47) having outer conductor diameter of 1.2 mm).

The instrument may include a retractable cover for the instrument tip, wherein, when the instrument tip is covered the instrument occupies a tissue penetrating configuration for introducing fluid invasively into the biological tissue, and when the instrument tip is exposed the instrument occupies a tissue treatment configuration for emitting RF EM radiation and/or microwave EM radiation. The cover may resemble a cone that can be pushed (e.g. by a guide wire extending alongside the coaxial cable) over the instrument tip.

The instrument tip may be curved in a direction between the side edges of the planar body. For example, it may have a spoon-like shape. It may be curved (or convex) at the bottom face and be curved upwards from the proximal to distal end of the structure.

Features of the first aspect of the invention mentioned above may also be applied to the second aspect of the invention.

In a development of both aspects, the instrument tip may be rotatable under the control of the device operator. In one embodiment, rotation may be achieved by turning the common carrier tube within the instrument channel of the endoscope, e.g. using a suitable handle or control knob. In another embodiment, the instrument tip body may be mounted on a rotatable plate that can turn e.g. by +/−90° relative to the common carrier tube. In this arrangement, the coaxial feed cable and fluid feed cable may be flexible to accommodate the movement of the first dielectric body during rotation. The rotatable plate may be turned by a pair of control wires which each operate a pivoting lever engaged with the plate.

Herein, the first frequency may be a stable fixed frequency in the range 10 kHz to 300 MHz and the second frequency may be a stable fixed frequency in the range 300 MHz to 100 GHz. The first frequency should be high enough to prevent the energy from causing nerve stimulation and low enough to prevent the energy from causing tissue blanching or unnecessary thermal margin or damage to the tissue structure. Preferred spot frequencies for the first energy source include any one or more of: 100 kHz, 250 kHz, 500 kHz, 1 MHz, 5 MHz. Preferred spot frequencies for the second energy source include 915 MHz, 2.45 GHz, 5.8 GHz, 14.5 GHz, 24 GHz.

BRIEF DESCRIPTION OF THE DRAWINGS

Embodiments of the invention are discussed in detail below with reference to the accompanying drawings, in which.

DETAILED DESCRIPTION

Further Options and Preferences

Figure 1:
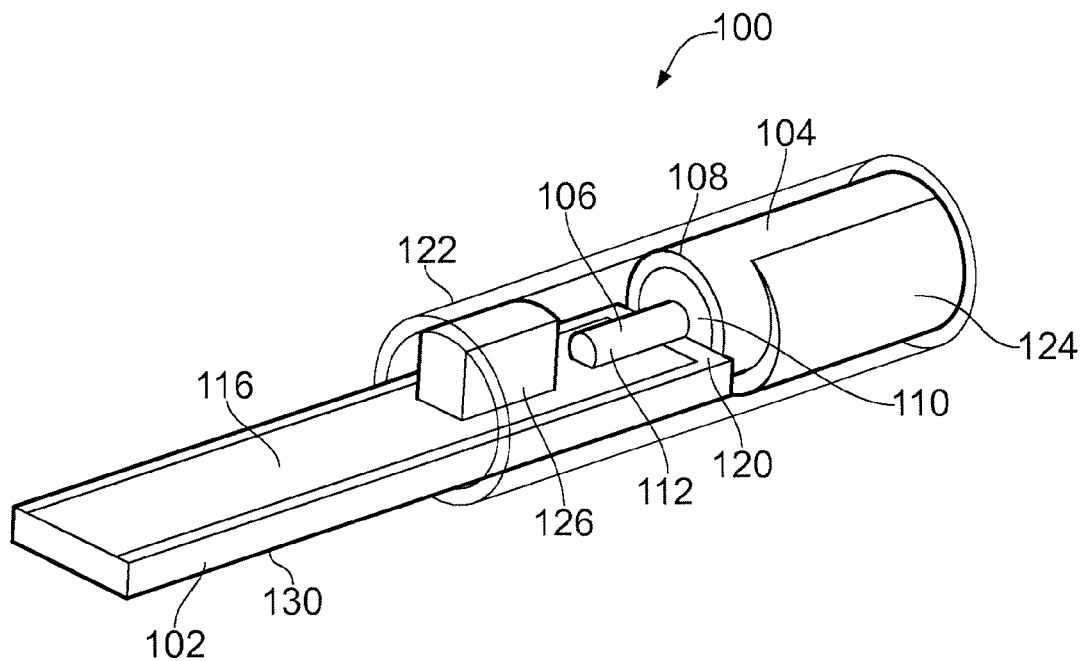
FIG. 1 is a top perspective view of a instrument that may be useful for understanding the invention.

As mentioned above, the disclosure herein relates to developments of a concept put forward in the applicant's earlier UK patent application no. 0912576.6, filed on 20 Jul. 2009, and incorporated herein by reference. UK patent application no. 0912576.6 describes an electrosurgical instrument in the form of a spatula comprising a planar transmission line for carrying microwave energy formed from a sheet of a first dielectric material having first and second conductive layers on opposite surfaces thereof, the planar transmission line being connected to a coaxial cable that is arranged to deliver microwave energy to the planar transmission line, the coaxial cable comprising an inner conductor, an outer conductor coaxial with the inner conductor, and a second dielectric material separating the outer and inner conductors, the inner and outer conductors extending beyond the second dielectric at a connection interface to overlap opposite surfaces of the transmission line and electrically contact the first conductive layer and second conductive layer respectively. The first conductive layer is spaced from the end of the transmission line that abuts the coaxial cable to electrically isolate the outer conductor from the first conductive layer and also the distance of the gap is involved with matching the impedance of the energy delivered from the microwave source with the impedance of the biological tissue, and the width of the first and second conductive layers is also selected to help create an impedance match between the transmission line and the coaxial cable. The spatula configuration set forth in UK patent application no. 0912576.6 provides desirable insertion loss between the co-axial feed line and the end radiating section, whilst also providing desirable return loss properties for the edges of the spatula when in contact with air and biological tissue respectively. In more detail, the insertion loss along the structure may be less than 0.2 dB at the frequency of interest, and the return loss less than (more negative than) −3 dB, preferably less than −10 dB. These properties may also indicate a well matched junction between the coaxial cable and the transmission line spatula structure, whereby microwave power is launched efficiently into the spatula. Similarly, when the edges of the spatula are exposed to air or biological tissue that is not of interest, the return loss may be substantially zero (i.e. very little power radiated into free space or undesirable tissue), whereas when in contact with desirable biological tissue the return loss may be less than (more negative than) −3 dB, preferably less than −10 dB (i.e. the majority of power in the spatula is transferred to the tissue). The instrument discussed in UK patent application no. 0912576.6 is intended to radiate microwave energy from the edges of the planar transmission line to cause localised tissue ablation or coagulation.

However, UK patent application no. 0912576.6 also discloses that the spatula discussed above may have an RF cutting portion integrated therewith. The RF cutting portion may be formed by using the first and second conductive layers mentioned above as active and return electrodes for RF energy. This arrangement may take advantage of the fact that the active and return electrodes are in close proximity to one another, thus setting up a preferential return path to enable local tissue cutting action to take place without the need for a remote return pad or a highly conductive liquid, i.e. saline, existing between the two electrodes.

In this example, the RF cutting portion may comprise a RF voltage source coupled to the planar transmission line, a frequency diplexer/duplexer unit (or signal adder) comprising a low pass filter to prevent the high frequency microwave energy from going back into the lower frequency RF energy source and a high pass filter to prevent the lower frequency RF energy from going back into the higher frequency microwave energy source. In one example, the frequency diplexer/duplexer may be used to enable the microwave and RF energy sources to be combined at the generator and delivered along a single channel, e.g. co-axial cable, waveguide assembly or twisted pair, to the spatula structure. The RF cutting energy may be delivered solely into the tissue or may be mixed or added with the microwave energy and delivered simultaneously to set up a blended mode of operation.

Figure 2:
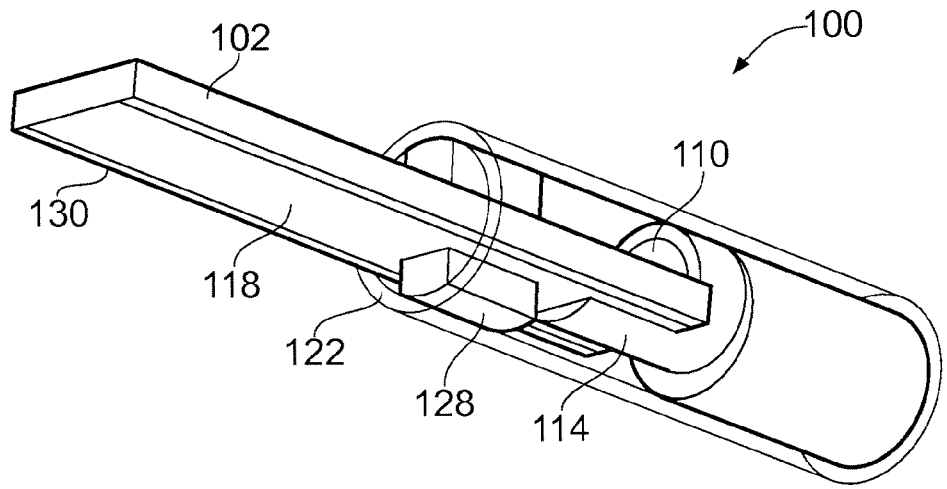
FIG. 2 is a bottom perspective view of the instrument shown in FIG. 1.

A detailed example of the spatula configuration having a bipolar antenna structure as described in UK patent application no. 0912576.6 is shown in FIGS. 1 and 2. FIG. 1 shows a instrument 100 having a 0.6 mm thick transmission line 102 connected to a coaxial cable 104. The instrument is suitable for operation at 2.45 GHz, 5.8 GHz and 14.5 GHz. The coaxial cable 104 comprises an inner conductor 106, an outer conductor 108 and a dielectric material 110 separating the inner and outer conductors 106, 108. At the distal end of the coaxial conductor 104, the inner and outer conductors 106, 108 have protruding portions 112, 114 which extend away from the dielectric material 110. The transmission line 102 is sandwiched between the protruding portions 112, 114 so that its proximal end abuts the distal end of the coaxial cable. The protruding portion 112 of the inner conductor is arranged to contact an upper conductive layer 116 of the transmission line 102 and the protruding portion 114 of the outer conductor is arranged to contact a lower conductive layer 118 of the transmission line 102.

A gap 120 is provided between the proximal edge of the upper conductive layer and the distal end of the coaxial cable to prevent shorting between the inner and outer conductors. The length of this gap also determines the impedance match between the source of microwave energy (generator, transmission line cable and radiating structure) and the biological tissue.

A plastic tube support 122 (shown as translucent for convenience) is mounted over the junction between the transmission line 102 and the coaxial cable 104. The inner diameter of the tube support 122 is greater than the outer diameter of the coaxial cable 104 to enable it to be fitted over the cable. A mounting structure 124, e.g. glue or the like, is attached between the coaxial cable 104 and the tube support 122 to secure the cable in place. Similarly, mounting blocks 126, 128 (e.g. glue) are attached between the transmission line 102 and the tube support 122 to secure the transmission line in place.

The transmission line may comprise of a 0.61 mm thick sheet 130 of TRF-41 (dielectric constant 4.1 and loss tangent 0.0035). The coaxial cable 104 has an outer diameter of about 2.2 mm and a pin diameter of 0.574 mm. The coaxial cable 280 used in a model set up to evaluate the microwave performance is UT 85C-LL (from Micro-Coax).

The conductive layers 116, 118 on the transmission line 102 go right to the distal end of the sheet 130 and are 2.002 mm wide. The sheet 130 is 2.6 mm wide.

The tube support 122 is a polypropylene tube having an outer diameter of 3.1 mm, to be a good sliding fit in an endoscope, and inner diameter of 2.6 mm. This gives a wall thickness of about 0.25 mm. The material and thickness is not critical; nylon or polyethene may be used, or a number of other plastics. The edges of the transmission line may preferably be chamfered so that the instrument will sit in place just below the diameter of the tube.

The tube comes 5 mm along the length of the transmission line 102. The overlap with the coaxial cable is 5 mm here but can be as long as required. The tube may be short enough to get through a bent endoscope. The main purpose of the tube is to support the instrument and to hold it steady in the end of the endoscope when a clinical procedure is taking place.

The mounting structure 124 and mounting blocks 126, 128 may be made of almost any material can hold the structure together mechanically, since this material (or materials) does not affect the performance of the device if kept away from the instrument edges and the pin of the coax.

The gap 120 between the upper conductive layer 116 and the coaxial cable is approximately 0.5 mm. This length is for maintaining a good impedance match between the radiating section (that forms a part of the microwave source) and the biological tissue.

The centre of the instrument is offset by about 0.5 mm (0.53 mm) from the centre of the coaxial cable. The axis of the outer tube is about 0.3 mm above the centre of the instrument, but only needs to fit over the components and hold them steady.

The dielectric sheet 130 may be just over one quarter or three quarters of a wavelength at the frequency of operation (e.g. 8 mm or 21 mm) so that a standing wave will not couple strongly to a supporting plastic tube near the base of the instrument. In theory, this length may be any of an odd multiple of a quarter of the wavelength at the frequency of operation.

Figure 3:
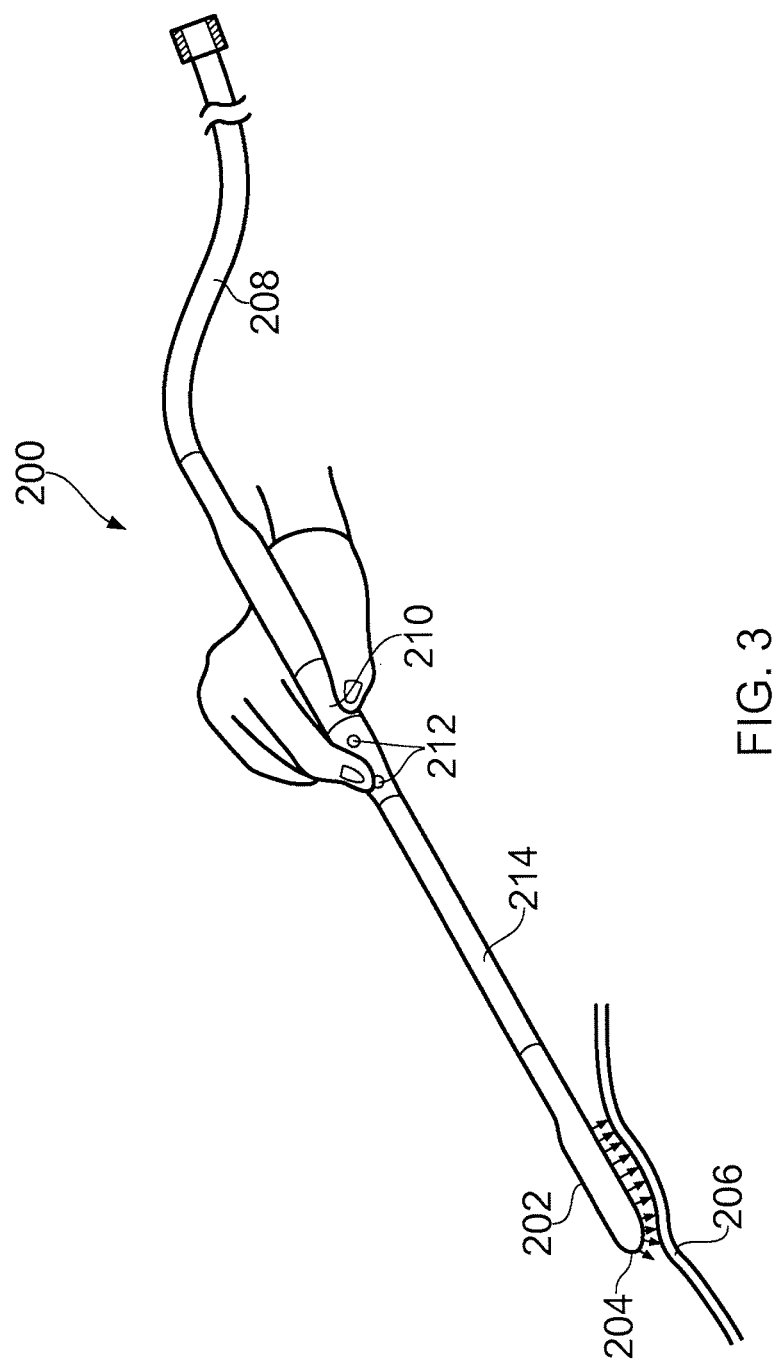
FIG. 3 is a schematic view of a blunt blade electrosurgical resection instrument that is an embodiment of the invention suitable for performing open surgical procedures.
Figure 12:
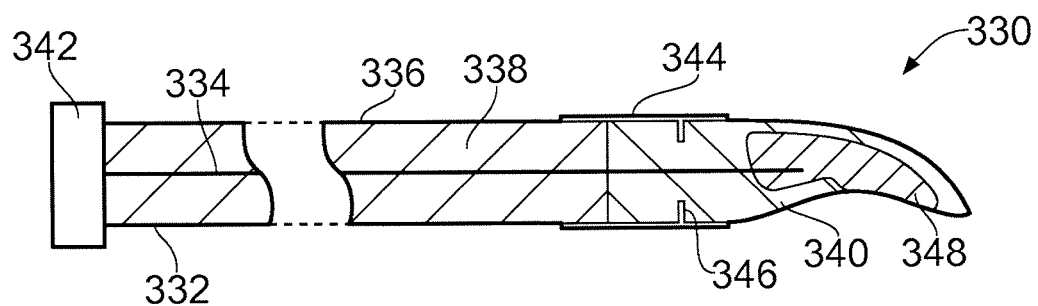
FIG. 12 is a schematic cross-sectional view through an electrosurgical resection instrument that is an embodiment of the invention suitable for use in gastrointestinal procedures.

FIG. 3 shows schematically an electrosurgical resection instrument 200 that is an embodiment of the invention. The instrument 200 may be used to coagulate and cut tissue. The instrument includes a instrument tip 202 (e.g. spatula or the like) producing electromagnetic fields 204 that are coupling into biological tissue 206 to cut through said tissue to remove sections of tissue (or complete organs) without loss of blood. A transmission line 208 feeds microwave and RF energy into the device. The user holds the device using an ergonomically designed handle 210 and may operate the device using push button switches 212 integrated into handle 210. Switches 212 may be used to activate RF and microwave sources independently or may be used to operate the device to deliver either or both energy sources automatically in accordance with the type and state of the contact tissue 206. A rigid section of transmission line cable 214 is used to transfer the microwave and RF energy from the hand piece section 210 into instrument tip 202. The instrument tip 202 illustrated is a unitary body comprising a single piece of metallised dielectric material, e.g. ceramic or the like, connected to the rigid transmission line cable 214, e.g. as shown in FIG. 12. However, any of the instrument tips discussed below may also be used in the device.

Figure 4A:
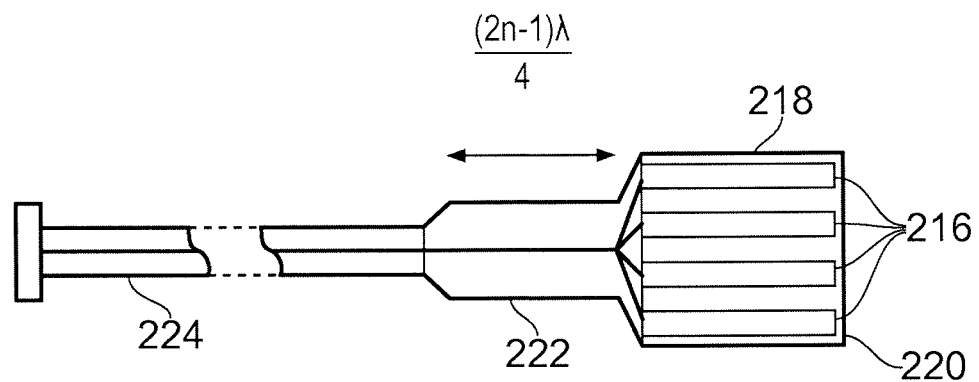
FIG. 4A is an electrosurgical resection instrument that combines a plurality of radiating blades as shown in FIGS. 1 and 2 that is an embodiment of the invention.
Figure 4B:
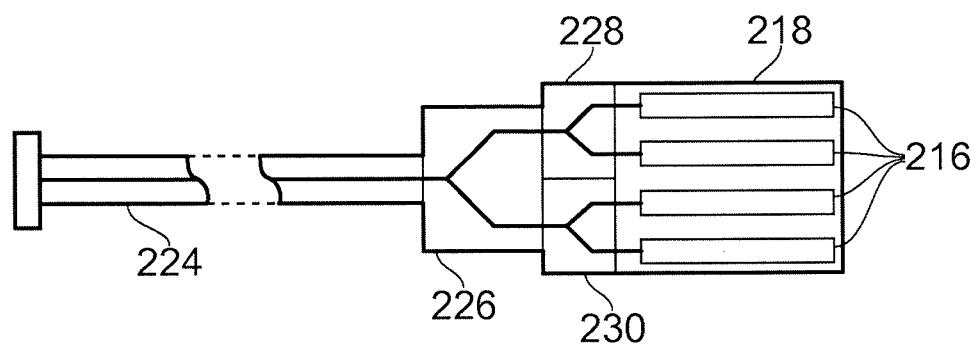
FIG. 4B is an electrosurgical resection instrument that combines a plurality of radiating blades as shown in FIGS. 1 and 2 that is another embodiment of the invention.

FIGS. 4A and 4B illustrate instrument tips that may be used in the design of an open surgical resection instrument, which use a plurality of spatula type instruments described above with reference to FIGS. 1 and 2. These instruments are fabricated onto a single substrate, and placed adjacent to one another to produce a composite structure with a longer radiating edge than that available from a single blade and capable of delivering uniform EM energy along the length of said composite structure. In these embodiments, the phase of the EM energy delivered from each blade is the same and whilst this is preferable, this invention is not limited to in-phase energy delivery.

FIG. 4A shows an arrangement that uses four radiating spatulas 216 positioned adjacent to one another that are fabricated onto a common substrate material 218, which may be quartz or another low loss microwave dielectric material, to produce a uniform field along the distal radiating edge 220 of the composite structure. The spatulas themselves are designed to match well into a biological tissue load present at the distal end of the instrument. To match the spatulas to the source, a quarter wave impedance transformer 222 is used to match the impedance of a coaxial feed line 224 (which may be rigid transmission line cable 214 mentioned above), which is nominally 50Ω, to the impedance of the four radiating spatulas 216 connected in parallel. The quarter wave impedance transformer 222 shown here is produced from a section of coaxial transmission line with an impedance equal to the square root of impedance $Z_0$ of coaxial feed line 224 multiplied by impedance $Z_{sp}$ of four radiating spatulas 216 connected in parallel, i.e. impedance $Z_T$ (in Ω) of transformer 222 is given by:

$$Z_T = \sqrt{Z_0 \times \frac{Z_{sp}}{4}}.$$

The length of said impedance transformer 507 is equal to an odd multiple of a quarter of the wavelength (loaded by the dielectric constant of the dielectric material that separates the four coaxially arranged conductors, taking into account the interaction between the structure and air or tissue) at the frequency of operation.

The invention is not limited to the use of four parallel radiating spatulas. Instrument tips may be provided with two or more. In practice, the easiest way of joining the substrates of the radiating spatulas side-by-side would be to bond a metal shim across both conductors (i.e. on both surface of the substrate), which would form a parallel plate transmission line of just over four times the width, and of approximately a quarter of the characteristic impedance, i.e. around 12.5Ω. The width of individual blades is around 2.5 mm. Thus, the width of the radiating section of the composite instrument tip is around 10 mm.

FIG. 4B shows an alternative arrangement for ensuring that an equal amount of power is delivered to the four radiating spatulas 216. In this arrangement, three equal phase power splitters (or power dividers) 226, 228, 230 are used to divide the power available at the distal end of coaxial feed line 224 into four equal parts. The power splitters 228, 230 connected to the radiating spatulas 216 may be balanced couplers, so that any unmatched power, i.e. where the instrument tip is not in contact with tissue, will be diverted to the uncoupled port of the coupler. In the arrangement shown, a first 3 dB power splitter 226 divides the power delivered by coaxial feed line 224 into two equal parts with the same phase, and delivers this power into two further couplers or 3 dB splitters 228, 230, which further divides the power into four equal parts with the same phase. The four equal magnitude/phase power sources are fed into radiating spatulas 216 to form a surgical resection instrument tip with a radiating blade length equal to the sum of four individual spatulas. The four spatulas 216 are preferably fabricated onto a single substrate or dielectric material 218. This arrangement has the advantage that the four radiating spatulas 216 are electrically separated, which will help ensure that the electric field produced along the length of the radiating section is entirely uniform.

Figure 5:
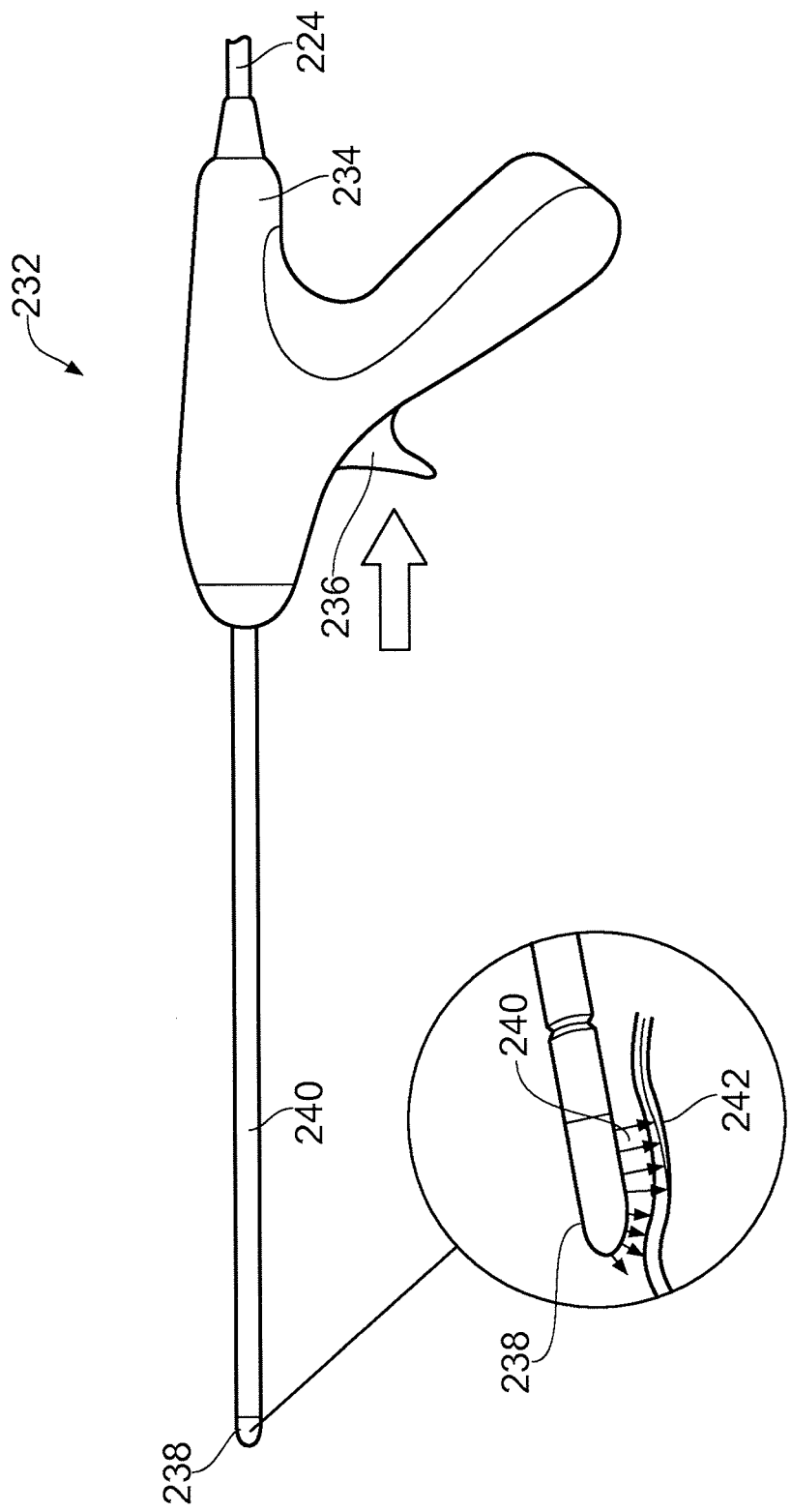
FIG. 5 is a schematic view of a laparoscopic version of an electrosurgical resection instrument that is an embodiment of the invention.

FIG. 5 illustrates a surgical resection instrument 232 suitable for carrying out laparoscopic surgery. The instrument comprises a handheld unit 234 that can be gripped in a user's hand. Microwave frequency energy and RF energy is fed from a generator (not shown) into the handheld unit 234 from coaxial feed cable 224. A trigger 236 is provided on the handheld unit 234. When the trigger 236 is depressed, the microwave frequency energy and/or RF energy is transferred to the instrument tip 238 via shaft 240, which contains a coaxial feed line. The instrument tip 238 illustrated is a unitary body comprising a single piece of metallised dielectric material, e.g. ceramic or the like, connected to the coaxial feed line in the shaft 240. The instrument tip 238 may be configured as shown in FIG. 12 below. However, any of the instrument tips discussed herein may be used. The microwave frequency energy and RF energy received at the instrument tip 238 produce fields 240 that couple into biological tissue 242 to coagulate and cut said tissue. The shaft 240 may be up to 2 m in length, i.e. 3.5 m, and have a diameter less than 5 mm and greater than 2 mm. The shaft 240 may be a flexible semi-rigid member suitable for use with an endoscopic device. This instrument may be suitable for key-hole surgery, which may include introducing it through a cannula.

Figure 6:
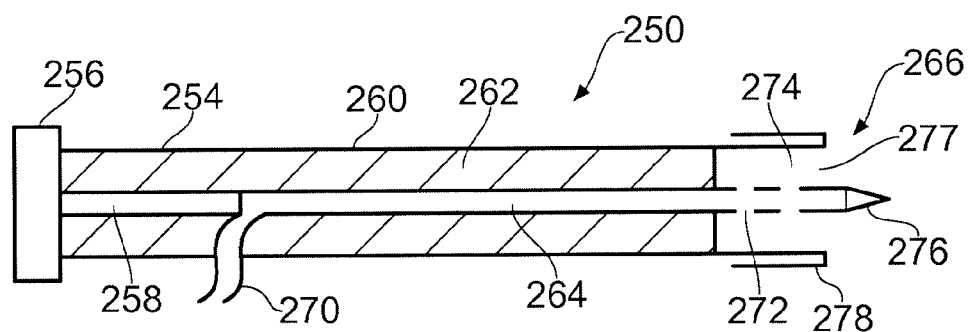
FIG. 6 is a cross-section view of an electrosurgical resection instrument having a coaxial structure that is an embodiment of the invention.
Figure 7:
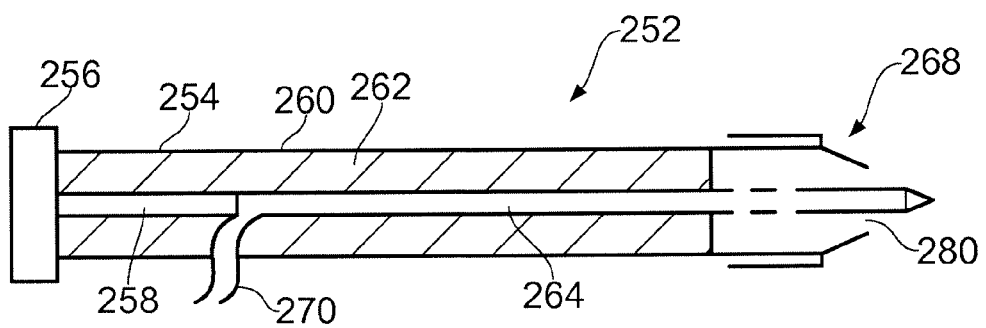
FIG. 7 is a cross-section view of an electrosurgical resection instrument having a coaxial structure that is another embodiment of the invention.

FIGS. 6 and 7 show two coaxial instrument structures 250, 252 that may be used to cut, coagulate, ablate and sterilise biological tissue. The overall diameter of these structures may range from less than 1 mm to greater than 5 mm. In both cases, the instrument structures 250, 252 comprise a coaxial feed line 254 having a connector 256 at a proximal end to receive microwave frequency energy and RF energy from a generator (not shown) via a flexible coaxial cable (not shown). The coaxial feed line 254 has an inner conductor 258 separated from and coaxial with an outer conductor 260 by a suitably low loss dielectric material 262, which may be low density PTFE, a micro-porous material such as Gortex® or the like.

In this embodiment, a distal portion of the inner conductor 258 is hollowed out to form a passageway 264 extending toward the instrument tip 266, 268. It is possible to make inner conductor 258 hollow by making use of the skin effect in conductors that occurs at microwave frequencies. When a conductive material is exposed to an EM field, it is subjected to a current density caused by moving charges. Good conductors, such as gold, silver and copper, are those in which the density of free charges are negligible and the conduction current is proportional to the electric field through the conductivity, and the displacement current is negligible with respect to the conduction current. The propagation of an EM field inside such a conductor is governed by the diffusion equation, to which Maxwell's equations reduce in this case. Solving the diffusion equation, which is valid mainly for good conductors, where the conduction current is large with respect to the displacement current, it can be seen that the amplitude of the fields decay exponentially inside the material, where the decay parameter (δ) is described using the following equation:

$$\delta = \frac{1}{\sqrt{\frac{\omega\mu\sigma}{2}}},$$

wherein δ is known as the skin depth and is equal to the distance within the material at which the field is reduced to 1/e (approximately 37%) of the value it has at the interface, σ is the conductivity of the material, μ is the permeability of the material, and ω is the radian frequency or 2πf (where f is the frequency). From this, it can be seen that the skin depth decreases when the frequency of the microwave energy increases as it is inversely proportional to the square root of this frequency. It also decreases when the conductivity increases, i.e. the skin depth is smaller in a good conductor than it is in another less conductive material.

For the microwave frequencies of interest and the materials of interest for implementing the structures shown in FIGS. 6 and 7, the skin depth is around 1 μm, hence the inner conductor 258 used in the construction of the coaxial applicators described here require a wall thicknesses of only about 5 μm to enable most of the microwave field to propagate. This implies that a hollow centre conductor can be used without causing any change to the EM wave propagating along the structure.

A fluid feed inlet 270 is formed through the side of the coaxial feed line 254 to permit an external fluid (gas or liquid) supply to communicate with the passageway 264 to deliver fluid to the instrument tip 266, 268. Preferably, the fluid feed does not affect the electromagnetic field that has been set up in the co-axial transmission line structure. EM modelling is performed to determine optimal feed points where the EM field is unaffected. In one embodiment, gas is transported to the instrument tip 266, 268 of the structures.

In FIG. 6, the instrument tip 266 includes an outlet 272 from the passageway, which permits the gas to enter the interior of the instrument tip 266 in which the dielectric material 262 is removed, which may form a plasma generation region 274. In this particular arrangement, the outlet 272 comprises a plurality of slots on the inner conductor 258 within the plasma generation region 274. In the plasma generation region 274, the electric field set up by the microwave frequency EM energy and/or RF field ionises the gas to produce plasma in the same region. The plasma may be thermal or non-thermal and may be used to sterilise tissue, provide a local return path for the RF current, produce surface coagulation and/or assist with tissue cutting. The plasma may be formed in the cavity by initially using energy at the RF frequency to provide the voltage necessary to strike the plasma and then using energy at the microwave frequency to enable the plasma to be sustained. Where the distance between the outer surface of the inner conductor and the inner surface of the outer conductor is very small, i.e. less than 1 mm, the microwave field may be used to strike and maintain plasma. Similarly, it may only be necessary to use the RF field to produce both non-thermal plasma for sterilisation and thermal plasma for surface ablation and/or tissue cutting.

The distal end 276 of inner conductor 258 in the instrument tip 266 is a solid pointed section, which may take the form of a sharp needle with a small diameter, i.e. 0.5 mm or less, which may be particularly effective when performing tissue cutting. The distal end 277 of the plasma generation region 274 is open to permit plasma to be delivered out of the instrument.

A quarter wave (or odd multiple thereof) balun 278, comprising a third coaxial conductor that is shorted at its distal end and open at its proximal end is connected to the structure to prevent microwave currents from flowing back along the outer conductor 260 to the coaxial feed line 254, which can cause heating of tissue that is in contact with the outer surface of the coaxial feed line 254 or cause the profile of the microwave energy to become non-optimal, or produce an undesirable zone or region of coagulation.

The composition of the gas and its flow rate and delivery profile, together with the power level and profile of the supplied RF EM energy and/or microwave EM energy determines the type of plasma that is set up in plasma generation region 274 of the instrument and transferred into biological tissue.

The instrument 252 in FIG. 7 has a similar instrument tip structure to the instrument shown in FIG. 6 except that outer conductor 260 has been continued such that it ends closer to the distal end 276 of the inner conductor 258 in the instrument tip 268. Here the outer conductor 260 takes the form of a pointed cone at the distal end of the instrument tip 268. The slope of outer conductor may be at the same angle as the slope of the solid pointed section. A jet of plasma may be emitted through a small gap 280 that separates the inner conductor 258 from the outer conductor 260 in this region.

The instrument tip may be arranged such that the initial ionisation discharge or breakdown of the gas occurs between the distal end of the outer conductor 260 and the solid pointed section of the inner conductor 258. The solid pointed section may be cone shaped, which is a preferred structure for use in clinical procedures where it is necessary to directly guide the applicator through a number of tissue layers to the treatment site, i.e. for percutaneous insertion or where the applicator has to fit into a channel that is of similar diameter to that of the applicator, i.e. the instrument channel of a surgical endoscope.

Figure 8:
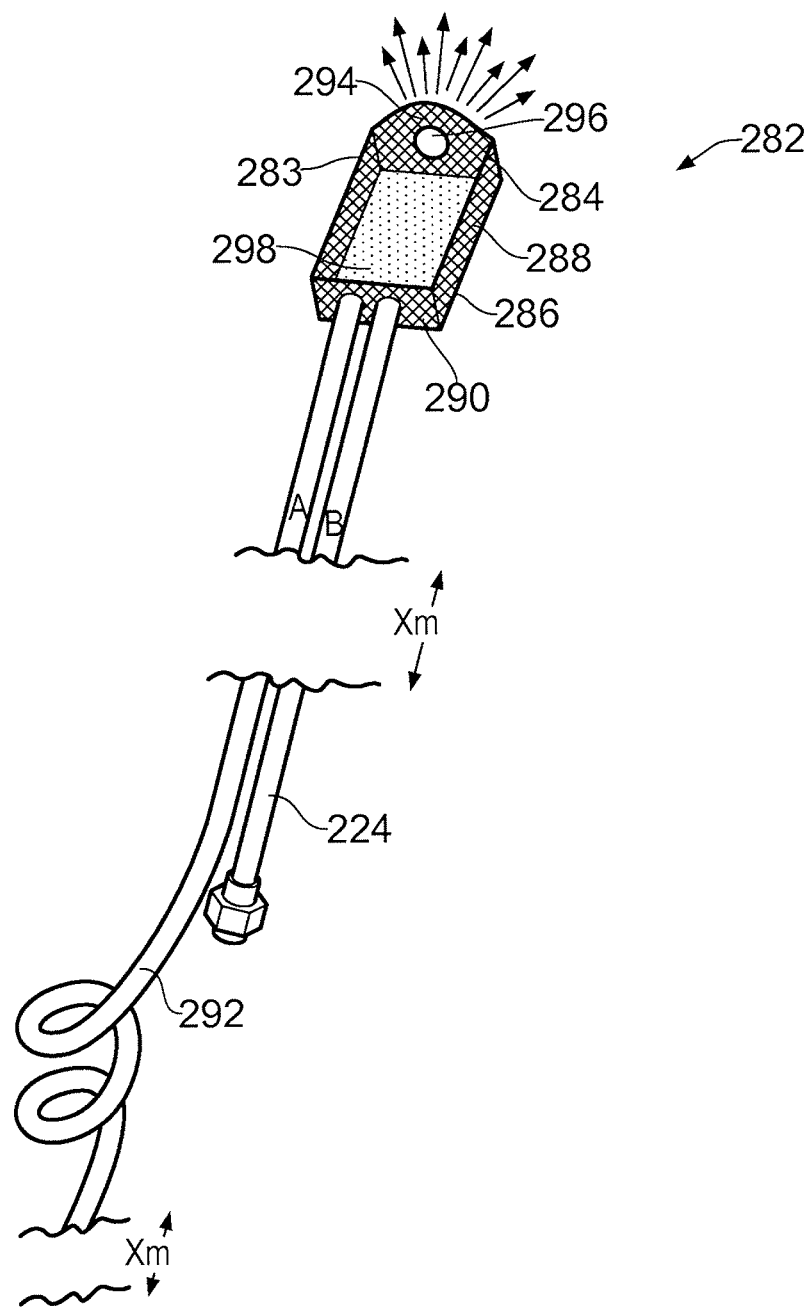
FIG. 8 is a schematic view of an open parallel plate electrosurgical resection instrument that is an embodiment of the invention.

FIG. 8 shows another instrument structure 282 that may be used to set-up/emit RF energy for tissue cutting, microwave energy for tissue coagulation/ablation or thermal/non-thermal plasma for sterilisation, surface coagulation/ablation, tissue cutting or to provide the preferential return path for the RF current to flow (which itself is generated by RF and/or microwave energy). This structure has a instrument tip 283 comprising a hollow parallel plate transmission line comprising: an upper conductive (e.g. metallic) plate 284 (shown transparent here for clarity), a lower conductive (e.g. metallic) plate 286, non-conductive side separator plates 288, non-conductive proximal end cover 290 with openings to allow coaxial feed line 224 and gas feed cable 292 to be attached and non-conductive distal end cover 294 with a slot or aperture 296 to allow thermal or non-thermal plasma to be emitted. The distance of separation between upper and lower plates 284, 286 may be less than 1 mm. The region between the plates may be filled with air, a gas (or gas mixture) from the gas feed 292, a liquid or a plasma 298. The plasma 298 may be generated by the electric field set up between the upper and lower plates 284, 286, which are connected to the inner and outer conductors of the coaxial feed line 224 respectively. The electric field may be an RF field or a microwave field or both delivered into the structure simultaneously or independently. The instrument tip 283 may be located several meters from the source of the RF and/or microwave frequency energy generator.

Figure 9:
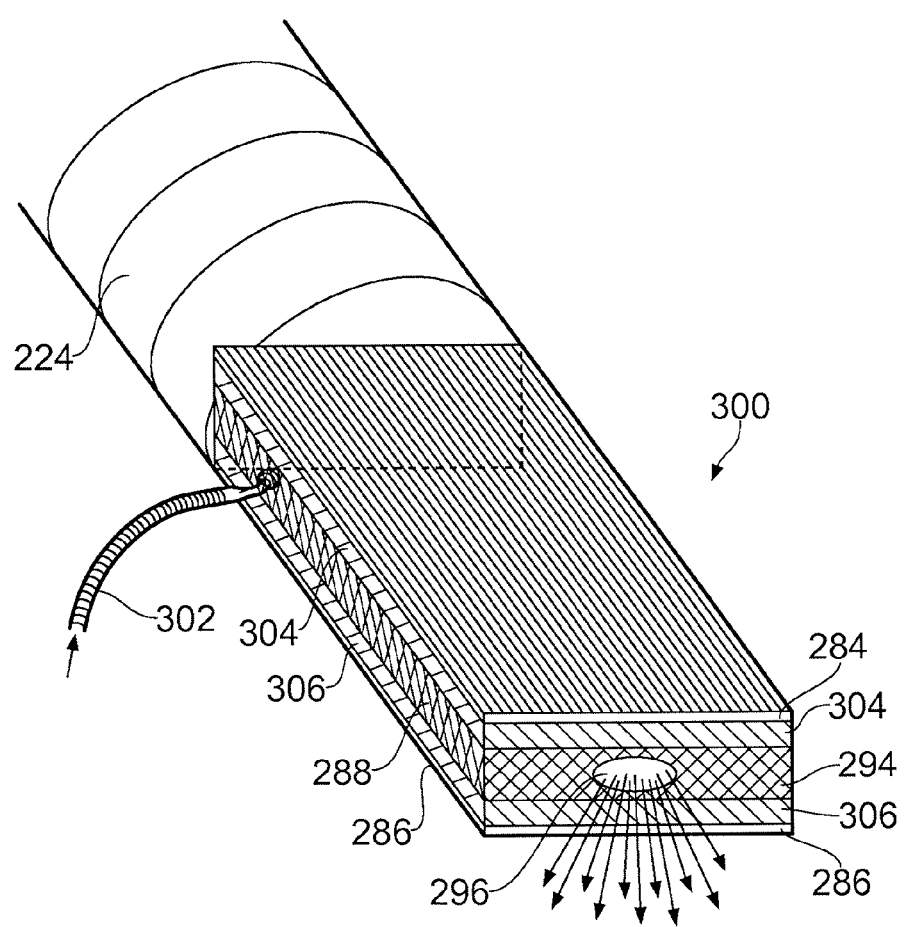
FIG. 9 is a schematic view of the instrument tip of the instrument shown in FIG. 8.

FIG. 9 illustrates in more detail a instrument tip 300 similar to the instrument tip 283 shown in FIG. 8. Features in common are given the same reference number and are not described again. This embodiment includes two additional layers of material within the instrument tip 300. These are layers of dielectric material 304, 306 formed on the inner surfaces of the upper and lower conductive plates 284, 286 respectively that can be used to concentrate the electric field or assist with the formation of plasma within the space (i.e. plasma generation region) enclosed by the walls of the instrument tip 300. The layers of dielectric material 304, 306 may be made from quartz or another suitable dielectric material having a high dielectric constant (or relative permittivity) so that they may also provide a local return path without the need to set up plasma.

The dielectric layers 304, 306 may be interchanged with their respective conductive plates 284, 286. For example, the upper and lower surfaces of the instrument tip 300 may be made from dielectric material having a layer of metallization on an inner surface thereof. In this configuration, the dielectric material acts as a support for the layer of metallization and does not take part on the electrical operation of the circuit. One layer of dielectric material between the two electrodes or layers of metallization may help focus the electric field and may enable a local return path to be set-up without the need to create plasma. In this arrangement the gas feed pipe 302 enters the instrument tip 300 through an aperture in the side wall 288.

Figure 10:
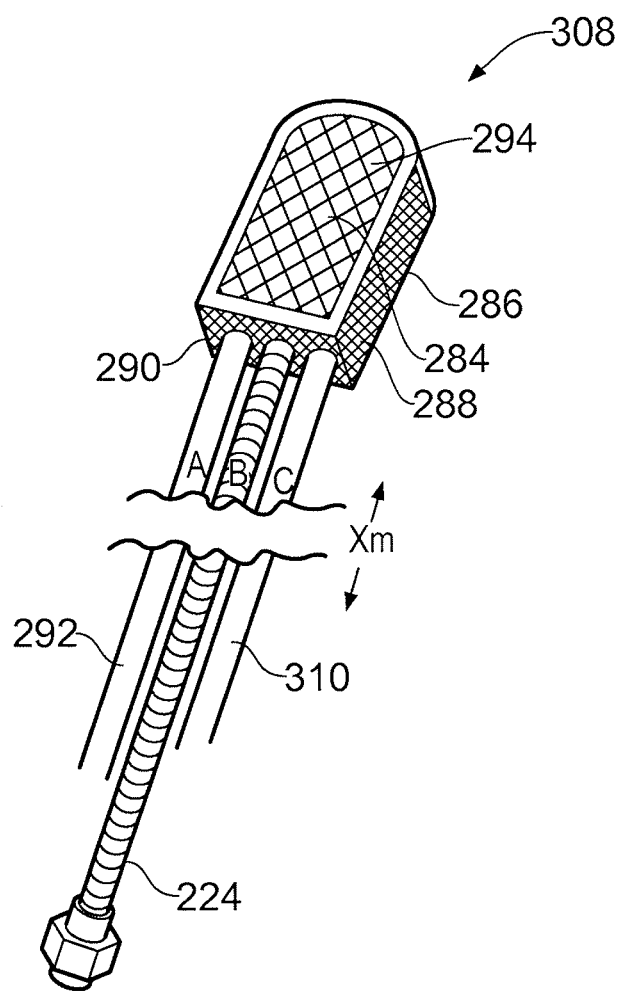
FIG. 10 is a schematic view of a closed parallel plate electrosurgical resection instrument that is an embodiment of the invention.

FIG. 10 is another embodiment of the invention that is based on a hollow (i.e. gas-filled) parallel plate transmission line. In this embodiment, the instrument tip 308 is closed, i.e. gas or plasma is not emitted therefrom. Instead, a separate gas pipe 310 is provided to allow the gas to be returned to the gas supply and recycled or released. Otherwise, the structure is similar to the instrument tip 282 shown in FIG. 8, and features in common are given the same reference number and are not described again.

In addition, this structure also includes a layer of dielectric material (not shown) with a non-finite thickness that extends between the upper and lower conductive plates 284, 286 to reduce the size of the plasma generation region and effectively to control the capacitance of the structure. If the area occupied by the fixed dielectric material is $A_1$, the area available to the gas (or plasma) is $A_2$, the dielectric constant of the fixed material is $\varepsilon_1$, the dielectric constant of the material filling the open space between the two plates is $\varepsilon_2$, and the distance of separation between the two plates is d, then, since the capacitance formed by the two regions are in parallel, the total capacitance $C_T$ may be expressed as:

$$C_T = \frac{\varepsilon_0(\varepsilon_1 A_1 + \varepsilon_2 A_2)}{d}.$$

Given the resistance of the parallel plate capacitor is the leakage resistance, which is extremely high, i.e. 10 MΩ, the impedance of the structure is approximately the capacitive reactance $X_C$, which can be expressed as:

$$X_C = \frac{d}{2\pi f \varepsilon_0 (\varepsilon_1 A_1 + \varepsilon_2 A_2)},$$

where f is the frequency of operation.

This implies that if the region enclosed by air, gas or plasma is much smaller than the region enclosed by the fixed value dielectric material and the dielectric constant (or relative permittivity) of said material is high, i.e. 4 or more, and the distance between the two plates is small, i.e. less than 1 mm, then the structure will provide the necessary local return path for the RF current without requiring plasma to exist between the two plates in order to provide the necessary conductive path.

It also implies that the capacitance or impedance of the overall structure may not change significantly when the gas/air is ionised and the plasma is formed. This means that non-thermal or thermal plasma can still be generated within the structure for tissue sterilisation, surface coagulation or tissue cutting, but the structure can also be used to support the delivery of RF energy and microwave energy into tissue to perform tissue cutting and coagulation without the need for plasma to be present within the structure. This may be advantageous in terms of there being no need to supply a microwave field to the structure to sustain plasma needed to provide a local return path when delivering RF energy into tissue to enable the device to perform tissue cutting.

Figure 11:
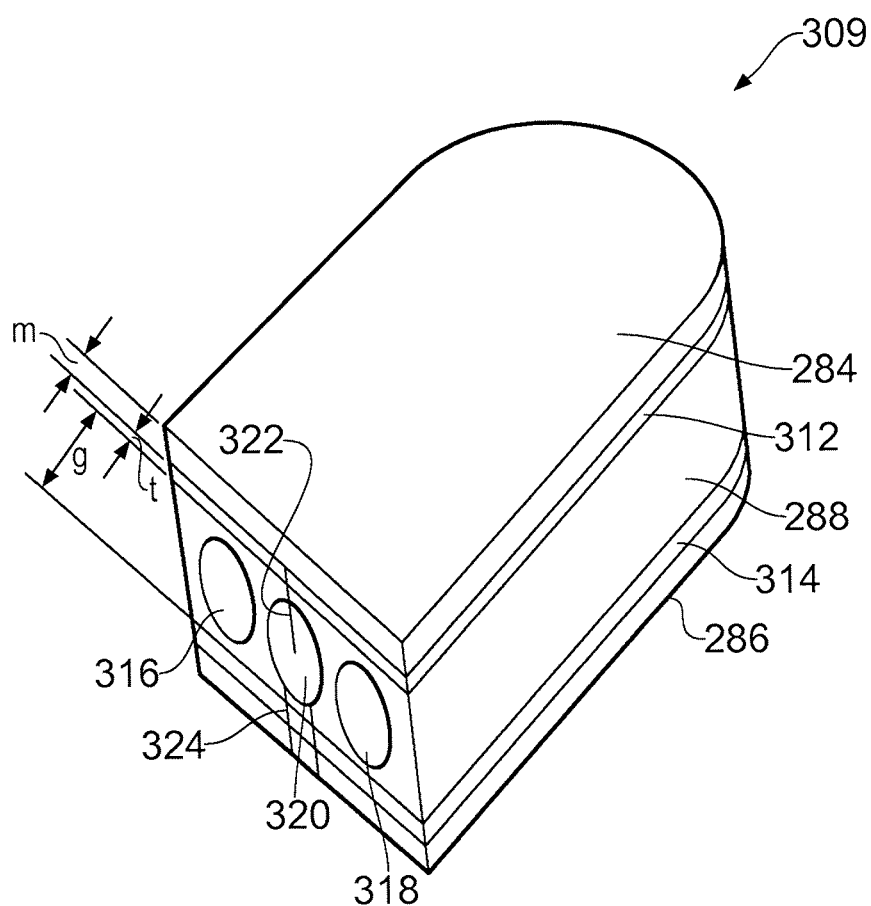
FIG. 11 is rear schematic view of the instrument tip of the instrument shown in FIG. 10, which shows the gas and RF/microwave energy feeds and the relative thickness of the layers in the instrument tip.

FIG. 11 shows another closed instrument tip 309, similar to the one shown in FIG. 10. Features in common are given the same reference number and are not described again. In this embodiment, the upper and lower conductive layers 284, 286 are metallisation layers formed on respective dielectric layers 312, 314 in a manner similar to that discussed above with reference to FIG. 9. In addition, FIG. 11 shows an inlet 316 and an outlet 318 for the gas, and a termination connection point 320 for the coaxial feed line (not shown) that transports the RF and microwave energy into the instrument tip. The termination connection point 320 includes a connector 322 for connecting the inner conductor of the coaxial feed line to the upper layer of metallisation 284 and a connector 324 for connecting the outer conductor of the coaxial feed line to the lower layer of metallisation 286.

FIG. 11 also indicates the thicknesses of layers used in the instrument tip. The layers of metallisation 284, 286 have a thickness m, and are generally the thinnest layers. The dielectric layers 312, 314 each have a thickness t. The separation (gap) between the dielectric layers 312, 314 has a height g, and is generally the thickest layer. The overall height of the instrument tip (i.e. 2m+2t+g) is preferably less than 2 mm and may be less than 1 mm. The relative sizes of the layer may obey the following relations:

m<t m<<g t<g

There are a number of modes of operation associated with the instrument structures described above with reference to FIGS. 6 to 11, where any combination of microwave energy, RF energy and gas can be selectively supplied separately or in any combination to the instrument tip. The possible modes of operation are as follows:

RF signal only (for biological tissue cutting). A local return path for the RF current may be provided within the instrument tip by suitable configuration of a bipolar emitting structure, i.e. thin layers of dielectric material with suitable dielectric constants.

RF signal and gas (for biological tissue cutting). The RF EM energy may be used with a gas to create a thermal plasma, which may be used to cut biological tissue.

RF signal and gas (for tissue sterilisation). The RF EM energy may be used with a gas to create a non-thermal plasma, which may be used to sterilise biological tissue. The sterilisation may occur at the same time as the RF energy is used to cut the tissue.

RF signal and gas (for surface coagulation or ablation). The RF EM energy may be used with a gas to create a thermal plasma, which may be used to perform tissue surface coagulation or ablation.

microwave signal only (for coagulation or ablation). The instrument tip may act as an antenna to radiate microwave frequency EM energy into tissue to perform coagulation and/or ablation.

microwave signal and gas (for biological tissue cutting). The microwave frequency EM energy may be used with a gas to create a thermal plasma, which may be used to cut biological tissue.

microwave signal and gas (for tissue sterilisation). The microwave frequency EM energy may be used with a gas to create a non-thermal plasma, which may be used to sterilise biological tissue. The sterilisation may occur at the same time as the microwave frequency EM energy is used to perform coagulation and/or ablation.

microwave signal and gas (for coagulation or ablation). The microwave frequency EM energy may be used with a gas to create thermal plasma, which may be used to perform surface coagulation or ablation.

RF signal and microwave signal (for coagulation or ablation). The RF signal may be used to assist the microwave energy with tissue ablation or coagulation.

RF signal, microwave signal and gas (for biological tissue cutting). The RF EM energy and microwave frequency EM energy may be used in combination with a gas to create a thermal plasma, which may be used to cut tissue.

RF signal, microwave signal and gas (for tissue sterilisation). The RF EM energy and microwave frequency EM energy may be used in combination with a gas to create a non-thermal plasma, which may be used to sterilise biological tissue.

RF signal, microwave signal and gas (for coagulation or ablation). The RF EM energy and microwave frequency EM energy may be used in combination with a gas to create a thermal plasma, which may be used to perform surface coagulation or ablation.

It is possible for the device to be switched between thermal delivery and non-thermal plasma by adjusting the microwave and/or RF source or by changing the flow rate of the gas, the gas mixture or the gas delivery profile.

The RF energy may be used to cut tissue and plasma formed by use of the RF energy and/or the microwave energy may be used to provide the local return path for the RF current needed to cut tissue.

The microwave and RF energy may be applied to the structure simultaneously, where the RF energy is being used to cut the tissue and the microwave energy is being used to sustain the plasma used to create the preferential path for the RF current being used in the cutting process.

Figure 13:
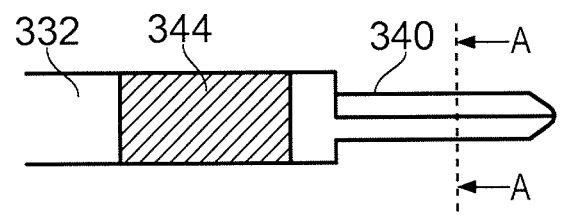
FIG. 13 is a schematic plan view of the instrument tip of the instrument shown in FIG. 12.
Figure 14:
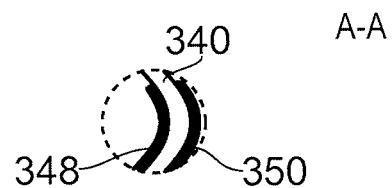
FIG. 14 is a schematic cross-sectional view through the hooked portion of the instrument tip shown in FIG. 13.

FIGS. 12 to 14 depict an electrosurgical instrument 330 that is an embodiment of the invention particularly suited to use in gastrointestinal procedures. The instrument 330 comprises a coaxial feed line 332 having an inner conductor 334 separated from and coaxial with an outer conductor 336 by a dielectric material 338. A instrument tip 340 is connected at the distal end of the coaxial feed line 332. A connector 342 is connected to the proximal end of the coaxial cable to receive RF EM energy and microwave frequency EM energy from a source (e.g. via a flexible coaxial cable).

The instrument tip 340 is a unitary piece of dielectric material (e.g. low loss Dynallox® Alumina) having two separate layers of metallisation formed thereon. The inner conductor 334 of the coaxial feed line 332 extends beyond the distal end of the coaxial feed line 332 into the interior of the instrument tip 340. From there it is electrically connected to one of the layers of metallisation. The outer conductor 336 of the coaxial feed line 332 is connected to the other layer of metallisation. The instrument tip 340 is fixed to the coaxial feed line 332 by a sleeve 344 (e.g. of stainless steel), which may be crimped to force securing tabs 346 into corresponding notches in the ceramic body of the instrument tip 340. The length of the sleeve 344 may be selected to match the impedance of the instrument tip 340 to the coaxial feed line 332, i.e. it may act as a tuning stub.

The layers of metallisation 348, 350 are provided on the side surfaces of the instrument tip 340 (see FIG. 14). The layers are separated from each other by the ceramic so that it effectively forms a planar transmission line, similar to the structures discussed above. In this embodiment, the layers of metallisation are set back from the side edges and the distal edge of the instrument tip except at regions where it is desired to emit an RF EM field. FIG. 12 shows schematically a first layer of metallisation 348 which is set back slightly from the edges of the instrument tip except along a region along the bottom edge.

In this embodiment, the instrument tip 340 has a hooked shape where one of the edges of the instrument tip 340 curves inwards and outwards, i.e. defines a recess. The recess may include a substantially proximally facing surface for facilitating tissue removal, e.g. by permitting tissue to be pulled, scooped or scraped away from the treatment site. The region along the bottom edge (the RF cutting region) to which the first layer of metallisation 348 extends is on the inside of the recess.

The length of the instrument tip 340 that extends from the sleeve 344 to deliver RF and microwave energy may be between 3 mm and 8 mm, preferably 4 mm. The width of the instrument tip may be similar to the diameter of the coaxial feed line, e.g. between 1.1 mm and 1.8 mm, preferably 1.2 mm. The thickness of the distal part of the instrument tip 340 may be between 0.2 mm and 0.5 mm, preferably 0.3 mm (see FIG. 14).

The general shape of the distal end of the instrument is of a spoon or scoop having a radius commensurate with that of the inner region of the vessel (e.g. bowel) in which treatment is to take place. For example, the curved arrangement shown may be suitable for getting underneath a polyp and scooping it out.

FIG. 13 shows a plan view of the instrument tip 340. The distal end is bevelled. FIG. 14 is a cross-section taken along the line A-A in FIG. 13, and shows the curved nature of the instrument tip 340.

The instrument 330 may be rotatable when inside the bowel, e.g. using one of the mechanisms described below with reference to FIGS. 22 to 25.

The instrument may incorporate fluid feed conduit (not shown) to provide a liquid (e.g. saline) injection capability. For example, the saline could be introduced along the inner conductor of the coaxial feed line in a manner similar to the embodiments shown in FIGS. 6 and 7, to be injectable out of an aperture formed in the instrument tip 340. Alternatively a separate fluid feed conduit may be mounted alongside the coaxial feed line. This idea of an integrated instrument and saline applicator may be particularly useful for removing sessile polyps which do not have a stalk from the bowel wall. In this procedure, the bowel wall (the submucosal layer) may be injected with saline (or other fluid) to provide a barrier (in which the applied RF or microwave EM energy would be exclusively dissipated) when removing the polyp. The advantages of this method are that it may reduce the risk of the energy being delivered too far into bowel wall thereby causing perforation, and that it may enable the diseased tissue being removed not to be damaged, so that histology can be performed on it.

A instrument for treating polyps in the bowel having the fluid delivery function describe above may thus perform any of the following actions:

injection of fluid (saline or other) to plump up the wall of the bowel to reduce risk of bowel perforation. It is advantageous to be able to use same instrument to deliver fluid as delivers RF and/or microwave energy since deflation may occur when a separate instrument is introduced into the region due to the fluid seeping out or deflation may occur during treatment. The ability to introduce fluid using the same treatment structure enables the level to be topped up as soon as deflation occurs.

injection of fluid to flush out the bowel. The same instrument may be used to introduce fluid (water, saline, etc) into the bowel to remove waste products that reside inside the bowel to provide better visibility during treatment.

applying RF EM energy to cutting through the polyp.

applying microwave EM energy to coagulate the blood to prevent excessive bleeding or to stem blood loss (which may also provide enhanced visibility)

applying microwave EM energy to ablate tissue. Cancerous polyps may be destroyed by ablation only or cancerous tissue left behind subsequent to polyp removal can be destroyed.

The ability to introduce fluid using the same treatment structure reduces risk, i.e. of infection, to the patient and enables the overall clinical procedure to be performed in a relatively short duration of time.

During treatment it may be necessary to withdraw the fluid feed when the RF or microwave energy is applied. For this purpose, a cone may be pushed over the instrument tip when fluid is required, and pulled back over the fluid feed conduit when fluid is not required. The cone (or other suitable retractable cover) may be controlled by one or more guide wires running along the assembly or it may be controlled by longitudinal movement of the fluid feed conduit.

Figure 15:
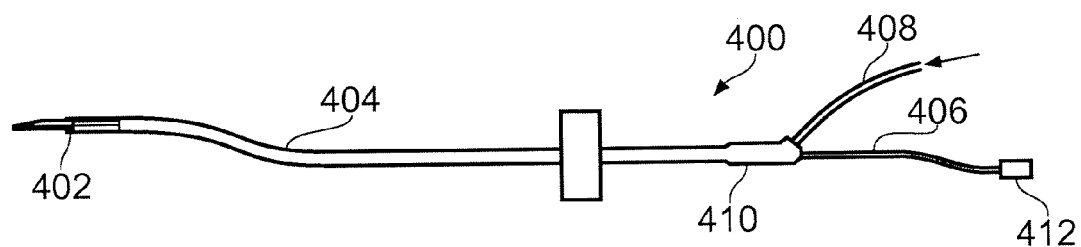
FIG. 15 is a schematic view of a complete electrosurgical assembly comprising an electrosurgical instrument that is an embodiment of the invention.

FIG. 15 shows a schematic side view of an electrosurgical apparatus 400 in which an electrosurgical instrument 402 that is an embodiment of the invention can be used. The apparatus 400 comprises a common carrier tube 404 which receives a coaxial cable 406 and a fluid feed conduit 408 at a junction element 410 located at its proximal end and conveys them to the instrument 402 at its distal end. The coaxial cable 406 is connected to a RF/microwave energy generator (not shown) via a quick release connector 412. In this embodiment, the fluid feed conduit 408 is arranged to receive saline solution, e.g. from a syringe (not shown). A rotation knob 414 is mounted on the common carrier tube 404 to enable it to be rotated when mounted in the instrument channel of an endoscope. This structure is discussed in more detail below with reference to FIG. 22.

Figure 16:
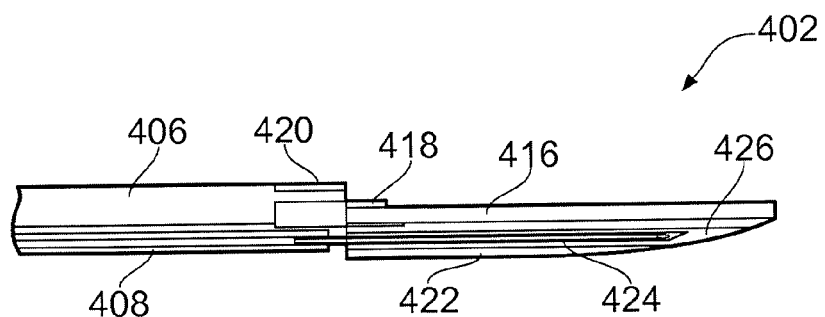
FIG. 16 is a schematic cross-sectional view through the electrosurgical instrument shown in FIG. 15.

The instrument 402 itself is shown in more detail in FIG. 16. The instrument tip body comprises a dielectric block 416 that has layers of metallisation on its upper and lower surfaces, similar to the arrangement discussed with reference to FIGS. 1 and 2. The inner conductor 418 of the coaxial cable 406 protrudes from the distal end of the coaxial cable 406 and is electrically bonded (e.g. using solder) to the upper layer of metallisation (first conductive element). The outer conductor of the coaxial cable 406 is electrically coupled to the lower layer of metallisation (second conductive element) by a braid termination 420. The braid termination 420 comprises a tubular part that is electrically bonded to the outer conductor and a distally extending plate part that fits under the dielectric block 416 and is electrically connected to the lower layer of metallisation.

In this embodiment, a shaped piece of dielectric material 422 is attached to the lower surface of the dielectric block 416. It may be secured to the lower layer of metallisation. The shaped piece of dielectric material 422 is curved such that in cross-section its lower surface describes the chord of a circle between the edges of the dielectric block 416. In the longitudinal direction, the shaped piece of dielectric material 422 comprises a proximal part with a constant cross-section and a distal part in which the underside gradually tapers (e.g. in a curved manner) towards the dielectric block 416.

In this embodiment, the fluid feed conduit 408 terminates with a needle 424 (e.g. a hypodermic needle) which has an outer diameter smaller than the fluid feed conduit 408 and which terminates with a sharp point for penetrates biological tissue. The needle 424 is retained in a longitudinal bore hole 426 through the shaped piece of dielectric material 422. Longitudinal movement of the fluid feed conduit 408 relative to the dielectric block 416 acts to extend and retract the needle 424 from the instrument tip body.

Figure 17:
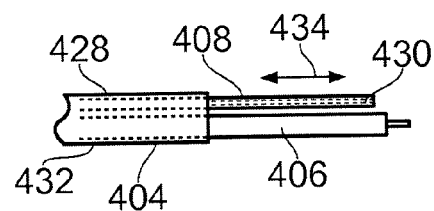
FIG. 17 is a schematic side view of the distal end of a common carrier tube suitable for use with the invention.

FIG. 17 shows the relationship between the fluid flow conduit 408, the coaxial cable 406 and the common carrier tube 404. The common carrier tube 404 is a flexible tube e.g. capable of insertion in and movement with an endoscope. A first longitudinal cavity 428 is formed in the common carrier tube 404 for holding the fluid feed conduit 408, which itself has a passageway 430 for conveying saline or other suitable fluid to the treatment site. The fluid feed conduit 408 may have freedom to move longitudinally along the first longitudinal cavity 428 as indicated by arrow 434. A second longitudinal cavity 432 is formed in the common carrier tube 404 for holding the coaxial feed cable 406.

Figure 18:
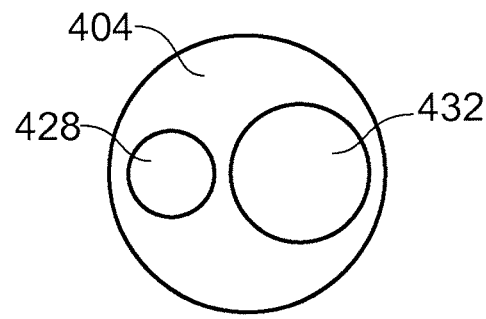
FIG. 18 is a schematic cross-sectional view through a first common carrier tube suitable for use with the invention.
Figure 19:
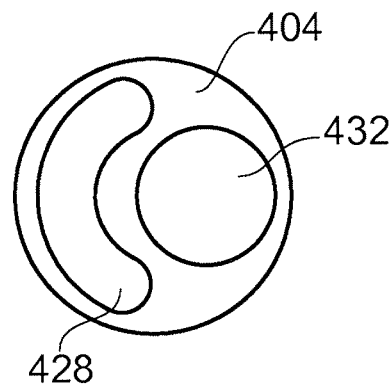
FIG. 19 is a schematic cross-sectional view through a second common carrier tube suitable for use with the invention.
Figure 20:
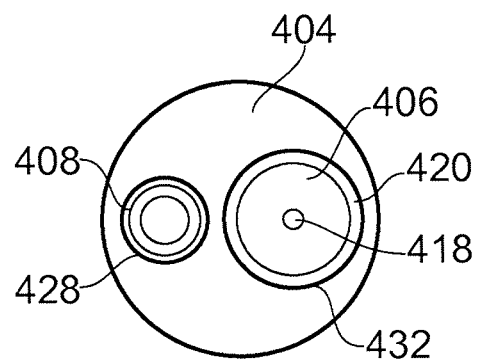
FIG. 20 is a schematic cross-sectional view through the common carrier tube of FIG. 18 conveying the fluid feed conduit and coaxial feed cable.

FIGS. 18 to 20 show cross-sectional views through various examples of a common carrier tube. FIG. 18 shows a first example in an empty state. The common carrier tube 404 is a solid cylindrical block of material having formed therein a first longitudinal cavity 428 for the fluid feed conduit and a second longitudinal cavity 432 for the coaxial cable. The cross-sections of the cavities in this example are circular, which allows the fluid feed conduit 408 and the coaxial feed cable 406 to fit snugly as shown in FIG. 20. In the this example, the diameter of the first longitudinal cavity 428 is less than the diameter of the second longitudinal cavity 432. For example, the first longitudinal cavity 428 may have a diameter of 0.8 mm and the second longitudinal cavity 432 may have a diameter of 1.3 mm. The diameter of the common carrier tube 404 itself is 2.5 mm or less, so that it fits in the instrument channel of an endoscope.

FIG. 19 shows a second example, in which the first longitudinal cavity 428 for the fluid feed conduit is non-circular. The first longitudinal cavity 428 in this case has a C-shaped cross-section, which may give it a larger cross-sectional area. This shape of cavity may be used if the cavity itself forms the fluid feed conduit, i.e. does not contain a further tube for carried the fluid.

FIG. 20 shows an example of the common carrier tube 404 in which the first and second longitudinal cavities 428, 432 have the fluid feed conduit 408 and coaxial feed cable 406 therein. The diameter of the second longitudinal cavity 432 is selected to accommodate the braid termination 420 on the outer surface of the coaxial feed cable 406.

Figure 21:
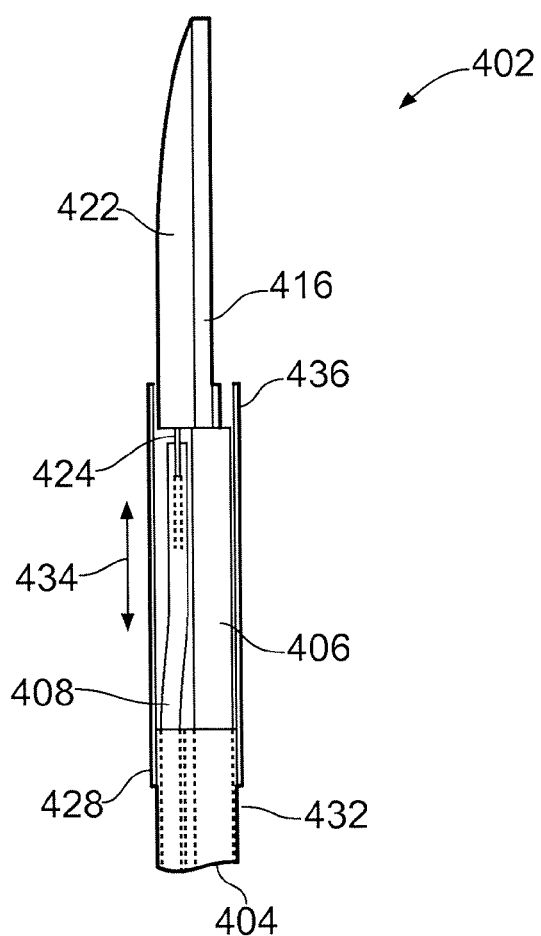
FIG. 21 is a schematic side view of an electrosurgical instrument that is an embodiment of the invention connected to a common carrier tube.

FIG. 21 shows the distal end of the apparatus shown in FIG. 15 from the distal end of the common carrier tube 404 to the tip of the instrument 402. In this example, the fluid feed conduit 408 and coaxial feed cable 406 extend out of the common carrier tube 404 by a short distance before they reach the instrument tip body. This feature, in conjunction with the flexibility of the fluid feed conduit 408 and coaxial feed cable 406, may permit the instrument tip body (and hence the cutting and/or radiating edges) to be manipulated, e.g. rotated, at the treatment site. The exposed parts of the fluid feed conduit 408 and coaxial feed cable 406 may be protected by a suitably rigid sheath 436, which is fixed to the common carrier tube 404.

Figure 22:
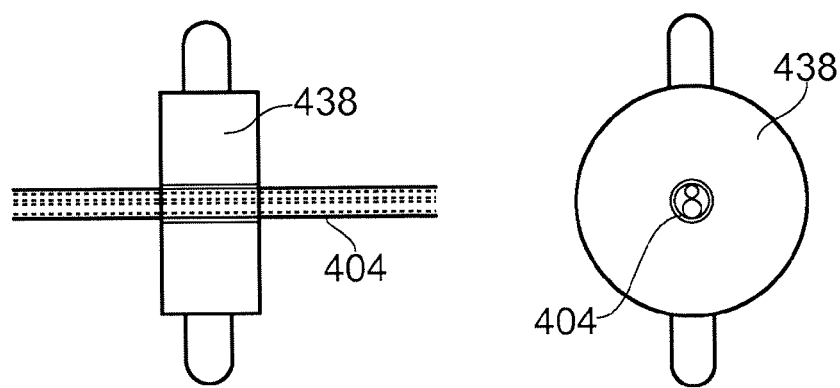
FIG. 22 is a side and end view of a rotator knob for use in an embodiment of the invention.

FIG. 22 shows a first mechanism for rotating the instrument tip body. Here, the outer surface of the common carrier tube 404 may be made slippery to facilitate slipping relative to the inner surface of the endoscope instrument channel. A rotation knob 438 may be secured (e.g. as a clamped over mould) on the common carrier tube 404 at its proximal end, which enables the operator physically to twist the whole assembly. In another embodiment, the rotation knob may be secured to the coaxial feed cable, which may be arranged to rotate within the common carrier tube.

Figure 23:
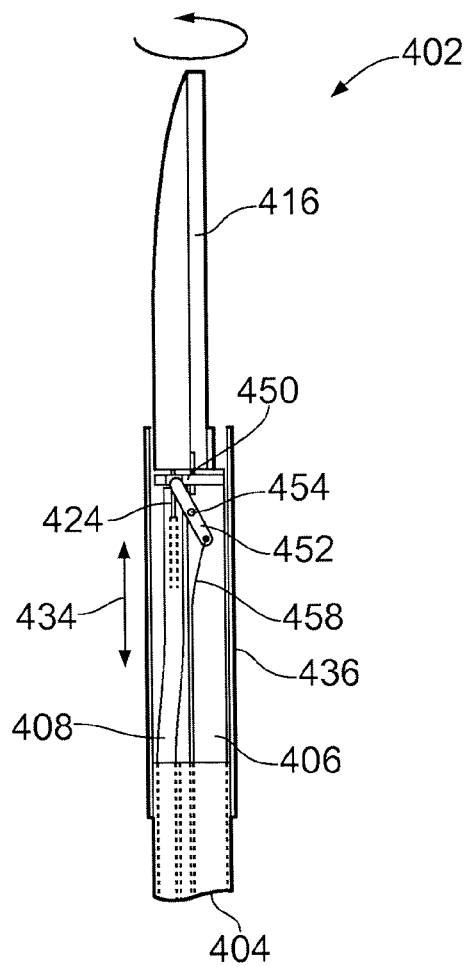
FIG. 23 is a schematic side view of a rotatable electrosurgical instrument that is an embodiment of the invention connected to a common carrier tube.
Figure 24:
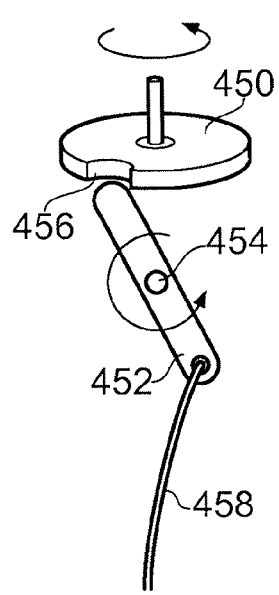
FIG. 24 is a schematic diagram illustrating the rotation mechanism used in the instrument shown in FIG. 23.
Figure 25:
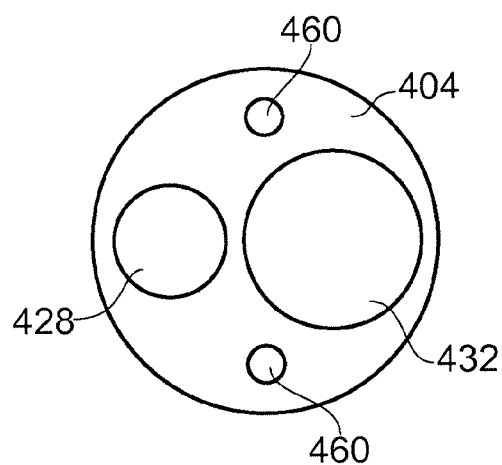
FIG. 25 is a schematic cross-sectional view through the common carrier tube used with the instrument shown in FIG. 23.

FIGS. 23 to 25 illustrate an alternative arrangement for rotating the instrument tip body. In this arrangement a rotary joint is provided at the proximal end of the instrument tip body. As shown in FIGS. 23 and 24, the rotary joint comprises a rotatable plate 450 whose rotation axis is aligned longitudinally with the common carrier cable, e.g. coaxial therewith. The rotatable plate 450 is secured to the instrument tip body and is rotatable about its rotation axis relative to the common carrier tube 404 through the action of one or more (preferably two) pivoting levers 452 (only one of which is shown in FIGS. 23 and 24 for clarity). Each pivoting lever 452 engages with the rotatable plate 450 (e.g. via a cooperating recess 456 or projection) such that movement of the lever about a pivot 454 causes the plate 450 to rotate. The lever 452 is moved by the operator using a control wire 458, which extends through the common carrier tube 404 to the outside of the device. Suitable bore holes 460 may be formed in the common carrier tube 404 for this purpose, as shown in FIG. 25.

Alternatively, a coaxial rotary joint may be used that enables both the inner and outer conductor to rotate, whilst maintaining good electrical contact without RF or microwave leakage. This joint may be manipulated using one or more guide wires mounted on a mechanical mechanism that can be used to rotate the radiating blade. This mechanism may form a part of the blade.

To assist in ensuring that the structure does not impede user manipulation of the endoscope when it is inserted inside the body, it is preferable for the coaxial cable to exhibit flexibility, e.g. by using a microwave transmission line cable with a micro-porous dielectric, e.g. a Gortex material, and by using a stranded material for the centre conductor rather than a solid material.

The devices described above may be particularly useful for performing Natural Orifice Transluminal Endoscopic Surgery (NOTES), where 'scarless' abdominal operations can be performed using an endoscope passed through one of the natural orifices within the body, i.e. mouth, urethra, anus, etc, then through an internal incision made in the stomach, vagina, bladder or colon, thus avoiding any external incisions or scars. The ability of the instruments shown in FIGS. 6 and 7 to perform surface ablation and sterilisation as well as tissue cutting and coagulation may make them particularly suitable for use in NOTES.

The invention claimed is:

1. An electrosurgical resection instrument for applying to biological tissue radiofrequency (RF) electromagnetic (EM) energy having a first frequency and microwave EM energy having a second frequency higher than the first frequency, the instrument comprising:
   an instrument tip comprising a body made of a first dielectric material separating a first conductive element from a second conductive element;
   a coaxial feed cable comprising an inner conductor, an outer conductor coaxial with the inner conductor, and a second dielectric material separating the outer conductor and the inner conductor, the coaxial feed cable being for conveying, simultaneously or separately, an RF signal having the first frequency and a microwave signal having the second frequency;
   a fluid feed conduit for delivering fluid to the instrument tip;
   wherein the inner conductor is electrically connected to the first conductive element and the outer conductor is electrically connected to the second conductive element to enable the instrument tip to receive the RF signal and the microwave signal, and
   wherein the first conductive element and the second conductive element are arranged to act:
      as an active electrode and a return electrode to convey RF EM radiation corresponding to the RF signal, and
      as an antenna to radiate microwave EM radiation corresponding to the microwave signal,
   wherein the fluid feed conduit is arranged to deliver liquid to the instrument tip, the fluid feed conduit having an outlet at the distal end of the instrument tip for introducing the liquid into the biological tissue,
   wherein the instrument tip further comprises a planar transmission line element in which the body of the first dielectric material is a substantially planar element, the first conductive element is a first conductive layer on a first surface of the substantial planar element, and the second conductive element is a second conductive layer on a second surface of the substantial planar element that is opposite to the first surface, and
   wherein the first surface of the substantially planar element and the second surface of the sustainably planer element extend between the first conductive element and the second conductive element in a direction parallel to a longitudinal axis of the coaxial feed cable;
   wherein both the first conductive layer and the second conductive layer extend up to at least one edge of the planer element in a region designated as an RF cutting portion, and are set back from the edges of the planer element except at the RF cutting portion; and
   wherein the instrument further comprises a common carrier tube for conveying the fluid flow conduit and the coaxial cable together to the instrument tip body.

2. The instrument according to claim 1, wherein both the first conductive element and the second conductive element extend to one or both edges of the first dielectric material.

3. The instrument according to claim 1, wherein the distal end of the first dielectric material is rounded.

4. The instrument according to claim 1, wherein the fluid feed conduit is arranged to deliver liquid saline to the instrument tip.

5. The instrument according to claim 1 comprising a third dielectric material mounted on the underside of the instrument tip body, the third dielectric member curving upwards along its length towards the instrument tip.

6. The instrument according to claim 5, wherein the third dielectric material includes a longitudinal passage for receiving the fluid feed conduit.

7. The instrument according to claim 1, wherein the fluid feed conduit comprises a tip section movable in a longitudinal direction relative to the instrument tip body between an extended position in which the outlet is located at the distal tip of the instrument, and a retracted position in which the outlet is set back from the distal tip of the instrument.

8. The instrument according to claim 7, wherein the tip section comprises a needle.

9. The instrument according to claim 1, wherein the common carrier tube has an outside diameter of less than 2.5 mm.

10. The instrument according to claim 9, wherein the common carrier tube comprises a first longitudinal bore for receiving the coaxial cable and a second longitudinal bore for receiving the fluid flow conduit.

11. The instrument according to claim 9 comprising a rotation knob secured to the common carrier tube for rotating the common carrier tube in an instrument channel of an endoscope.

12. The instrument according to claim 1, wherein the fluid feed conduit is arranged to deliver gas into a plasma generation region located between the first and second conductive elements in the instrument tip, and wherein the first conductive element and the second conductive element are configured to create an electric field from the received RF signal or the microwave signal that is capable of ionising the gas to generate a thermal or non-thermal plasma.

13. The instrument according to claim 12, wherein the plasma generation region either:
   is enclosed within the instrument tip, the plasma being used to provide a local return path for the RF signal to facilitate cutting the biological tissue, or
   includes an outlet for permitting non-thermal or thermal plasma to be delivered to the biological tissue.

14. The instrument according to claim 1, wherein the coaxial feed cable and the fluid feed conduit have a combined diameter that is less than 2.5 mm, and the instrument tip extends out of the coaxial feed cable by 12 mm or less, and has a width of 2.0 mm or less and a thickness of 0.5 mm or less.

15. The instrument according to claim 1, wherein the fluid feed conduit is arranged to deliver gas into a plasma generation region located between the first and second conductive elements in the instrument tip, and wherein the first conductive element and the second conductive element are configured to create an electric field from the received RF signal and the microwave signal that is capable of ionising the gas to generate a thermal or non-thermal plasma.

* * * * *